(12) United States Patent
Temelli et al.

(10) Patent No.: US 9,249,266 B2
(45) Date of Patent: Feb. 2, 2016

(54) SUPERCRITICAL FLUID TREATMENT OF HIGH MOLECULAR WEIGHT BIOPOLYMERS

(75) Inventors: Feral Temelli, Edmonton (CA); Bernhard Seifried, Edmonton (CA)

(73) Assignee: THE GOVERNORS OF THE UNIVERSITY OF ALBERTA, Edmonton, Alberta (CA)

( * ) Notice: Subject to any disclaimer, the term of this patent is extended or adjusted under 35 U.S.C. 154(b) by 112 days.

(21) Appl. No.: 13/638,254

(22) PCT Filed: Apr. 1, 2011

(86) PCT No.: PCT/CA2011/000360
§ 371 (c)(1),
(2), (4) Date: Dec. 20, 2012

(87) PCT Pub. No.: WO2011/120155
PCT Pub. Date: Oct. 6, 2011

(65) Prior Publication Data
US 2013/0101849 A1    Apr. 25, 2013

Related U.S. Application Data

(60) Provisional application No. 61/320,182, filed on Apr. 1, 2010.

(51) Int. Cl.
| | |
|---|---|
| *C08J 3/12* | (2006.01) |
| *A61K 9/50* | (2006.01) |
| *A61K 9/51* | (2006.01) |
| *C08J 3/215* | (2006.01) |
| *B29B 9/12* | (2006.01) |

(52) U.S. Cl.
CPC ............... *C08J 3/12* (2013.01); *A61K 9/5089* (2013.01); *A61K 9/5192* (2013.01); *B29B 9/12* (2013.01); *C08J 3/122* (2013.01); *C08J 3/215* (2013.01); *C08J 2305/00* (2013.01); *Y02P 20/544* (2015.11); *Y10T 428/2982* (2015.01)

(58) Field of Classification Search
USPC ............. 428/402, 403; 427/212; 536/123.12; 264/11, 4
IPC ....................... C08J 3/12; B29B 9/12
See application file for complete search history.

(56) References Cited

U.S. PATENT DOCUMENTS

| | | | |
|---|---|---|---|
| 2004/0110871 A1 | 6/2004 | Perrut et al. | |
| 2007/0120281 A1 * | 5/2007 | Khusid et al. | 264/11 |

FOREIGN PATENT DOCUMENTS

| | | | |
|---|---|---|---|
| WO | 95/01221 | | 1/1995 |
| WO | 96/00610 | | 1/1996 |
| WO | WO96/00610 | * | 1/1996 |
| WO | 2010150964 | | 12/2010 |
| WO | WO2010/150964 | * | 12/2010 |
| WO | 2011120155 | | 10/2011 |

OTHER PUBLICATIONS

A. Shariati, C.J. Peters, Recent developments in particle design using supercritical fluids. Curr. Opin. Solid State Mater. Sci. 7 (2003) 370-383.
Z. Knez, E. Weidner, Particles formation and particle design using supercritical fluids. Curr. Opin. Solid State Mater. Sci. 7 (2003) 353-361.
J. Jung, M. Perrut, Particle design using supercritical fluids: Literature and patent survey. J. Supercrit. Fluids 20 (2001) 179-219.
P. York, Strategies for particle design using supercritical fluid technologies. Pharm. Sci. Technol. Today 2 (1999) 430-440.
F. Mattea, A. Martin, A. Matias-Gago, M.J. Cocero, Supercritical antisolvent precipitation from an emulsion: beta-Carotene nanoparticle formation. J. Supercrit. Fluids 51 (2009) 238-247.
N. Ventosa, S. Sala, J. Veciana, DELOS process: a crystallization technique using compressed fluids: 1. Comparison to the GAS crystallization method. J. Supercrit. Fluids 26 (2003) 33-45.
N. Jovanović, A. Bouchard, G.W. Hofland, G.J. Witkamp, D.J.A. Crommelin, W. Jiskoot, Stabilization of proteins in dry powder formulations using supercritical fluid technology. Pharm. Res. 21 (2004) 1955-1969.
A. Bouchard, N. Jovanović, W. Jiskoot, E. Mendes, G.J. Witkamp, D.J.A. Crommelin, G.W. Hofland, Lysozyme particle formation during supercritical fluid drying: Particle morphology and molecular integrity. J. Supercrit. Fluids 40 (2007) 293-307.
A. Bouchard, N. Jovanović, G.W. Hofland, W. Jiskoot, E. Mendes, D.J.A. Crommelin, G.J. Witkamp, Supercritical fluid drying of carbohydrates: Selection of suitable excipients and process conditions. Eur. J. Pharm. Biopharm. 68 (2008) 781-794.
A. Bouchard, N. Jovanović, A.H. de Boer, A. Martin, W. Jiskoot, D.J.A. Crommelin, G.W. Hofland, G.J. Witkamp, Effect of the spraying conditions and nozzle design on the shape and size distribution of particles obtained with supercritical fluid drying. Eur. J. Pharm. Biopharm. 70 (2008) 389-401.
A. Bouchard, N. Jovanović, A. Martin, G.W. Hofland, D.J.A. Crommelin, W. Jiskoot, G.J. Witkamp, Effect of the modifier on the particle formation and crystallisation behaviour during precipitation from aqueous solutions. J. Supercrit. Fluids 44 (2008) 409-421.

(Continued)

*Primary Examiner* — Leszek Kiliman
(74) *Attorney, Agent, or Firm* — Bennett Jones LLP

(57) ABSTRACT

Micro- and nano-sized particles, agglomerates and fibers are generated from high molecular weight water-soluble biopolymers applying supercritical fluid technology. A method of producing micro- or nanoparticles from an aqueous solution of a high molecular weight biopolymer includes the step of spraying the aqueous solution together with a mixture of a compressible gas and a water-soluble co-solvent/antisolvent into a pressurized chamber. The method may be adapted to impregnate the micro- or nanoparticles with a bioactive material. A method for microencapsulating a bioactive material with a biopolymer is also provided.

26 Claims, 15 Drawing Sheets

(56) References Cited

OTHER PUBLICATIONS

A. Martin, A. Bouchard, G.W. Hofland, G.J. Witkamp, M.J. Cocero, Mathematical modeling of the mass transfer from aqueous solutions in a supercritical fluid during particle formation. J. Supercrit. Fluids 41 (2007) 126-137.

J. Kluge, F. Fusaro, N. Casas, M. Mazzotti, G. Muhrer, Production of PLGA micro- and nanocomposites by supercritical fluid extraction of emulsions: I. Encapsulation of lysozyme. J. Supercrit. Fluids 50 (2009) 327-335.

J. Kluge, F. Fusaro, M. Mazzotti, G. Muhrer, Production of PLGA micro- and nanocomposites by supercritical fluid extraction of emulsions: II. Encapsulation of Ketoprofen. J. Supercrit. Fluids 50 (2009) 336-343.

S. Varona, S. Kareth, M.J. Cocero. Encapsulation of essentials oils using biopolymers for their use in ecological agriculture. In 9th International symposium on supercritical fluids 2009. Arcachon, France.

L. Garcia-Gonzalez, A.H. Geeraerd, S. Spilimbergo, K. Elst, L. Van Ginneken, J. Debevere, J.F. Van Impe, F. Devlieghere, High pressure carbon dioxide inactivation of microorganisms in foods: The past, the present and the future. Int. J. Food Microbiol. 117 (2007) 1-28.

J. Zhang, T.A. Davis, M.A. Matthews, M.J. Drews, M. LaBerge, Y.H. An, Sterilization using high-pressure carbon dioxide. J. Supercrit. Fluids 38 (2006) 354-372.

B.S. Ghotra, T. Vasanthan, F. Temelli, Rheological properties of aqueous blends of high purity barley b-glucan with high purity commercial food gums. Food Chemistry 117 (2009) 417-425.

M. Sun, F. Temelli, Supercritical carbon dioxide extraction of carotenoids from carrot using canola oil as a continuous co-solvent. J. Supercrit. Fluids 37 (2006) 397-408.

M.A. Rodrigues, J. Li, L. Padrela, A. Almeida, H.A. Matos, E.G. de Azevedo, Anti-solvent effect in the production of lysozyme nanoparticles by supercritical fluid-assisted atomization processes. J. Supercrit. Fluids 48 (2009) 253-260.

G. Brunner, S. Peter, On the solubility of glycerides and fatty acids in compressed gases in the presence of an entrainer. Sep. Sci. Technol. 17 (1982) 199-214.

\* cited by examiner

SUPERCRITICAL FLUID TREATMENT OF HIGH MOLECULAR WEIGHT BIOPOLYMERS

CROSS REFERENCE TO RELATED APPLICATIONS

This application is the National Phase of International Application No. PCT/CA2011/000360, filed Apr. 1, 2011, which claims the priority benefit of U.S. Provisional Patent Application No. 61/320,182 filed on Apr. 1, 2010, the contents of which are incorporated herein by reference.

FIELD OF THE INVENTION

The present invention is directed to methods of generating micro- and nano-sized particles, agglomerates and fibers from high molecular weight water-soluble biopolymers applying supercritical fluid technology. The invention further relates to the resulting products and methods of using the resulting products.

BACKGROUND

Particle formation using supercritical fluids has been researched for many decades, and has resulted in the development of numerous processes using the supercritical fluid (SCF) either as solvent, such as in the "rapid expansion of supercritical solutions" (RESS) process, as antisolvent in the "gas antisolvent" (GAS) process, or as co-solvent in the "depressurization of an expanded liquid organic solution" (DELOS) process. Numerous variations and further developments of particle formation processes have emerged [1-4]. However, many of these processes require organic solvents to dissolve the solute to be precipitated (US Patent application publication Ser. No. US 2004/0110871 A1 to Perrut et al.).

In International Publication Nos. WO 1995/01221 and WO 1996/00610, methods are described for the formation of particles based on the antisolvent method, in which an aqueous solution of a substance is contacted with a co-solvent (also referred to as modifier) (such as ethanol) and a supercritical fluid in a coaxial nozzle. As stated in WO 1996/00610, the supercritical fluid may optionally contain a low level of a co-solvent (i.e. ethanol), preferably not more than 20%. However, such a low level of co-solvent is not sufficient to precipitate high molecular weight biopolymers such as polysaccharides.

Another approach to form β-carotene nanoparticles was presented by Cocero et al. [5], which is based on the 'supercritical fluid extraction of emulsions' (SFEE) process, related to the GAS process. In the SFEE process, a nanoemulsion of an organic solvent (dichloromethane) carrying the solute is dispersed in water to form an oil-in-water emulsion and dried using supercritical $CO_2$ (SC—$CO_2$). Each droplet resembles a small GAS precipitator, where upon expansion with $CO_2$ and extraction of the organic solvent, ultrasmall particles suspended in water are formed with a final organic solvent concentration of about 1 ppm [5].

In the DELOS process [6], the solute is first dissolved in an organic solvent and a compressed fluid such as $CO_2$ is added to expand the solution at the desired temperature and pressure. Then, the expanded solution is rapidly depressurized to atmospheric conditions, resulting in the formation of submicron or micron sized solute crystals due to the very large temperature drop that occurs upon depressurization.

Particle formation processes are known for the treatment of aqueous solutions containing the solute, which are sprayed into a high pressure precipitation chamber together with pressurized $CO_2$ enriched with ethanol. This approach is often referred to as the supercritical fluid drying process, which has been applied to precipitate proteins [7], enzymes [8], lactose, maltose, trehalose, raffinose, cyclodextrin, low-molecular-weight dextrans, mid-molecular-weight dextrans up to about 68,800 g/mol, and inulin [9], forming free-flowing powders. The effect of spraying conditions and nozzle design as well as the influence of various co-solvents added to $CO_2$ on the shape and size distribution of particles obtained with supercritical fluid drying has been studied by Bouchard et al. [10, 11]. It was found that methanol and ethanol used as a co-solvent in the SCF drying process acted as antisolvent in the precipitation of glycine, phenylalanine and lysozyme, besides their role in enhancement of water solubility in SC—$CO_2$ and evaporative water removal, whereas 2-propanol and acetone did not act as an antisolvent and affected mainly the evaporative water removal [11]. Various nozzle configurations were tested as well in the SCF drying process, including a simple T-mixer with small inner diameter or coaxial converging nozzles, with and without mixing chamber, as well as with ultrasonic wave generator [10], which showed that the nozzle design, processing pressure and flow rates had a pronounced effect on particle size, whereas morphology was found to be more likely linked to the precipitation mechanism rather than the atomization process [10]. A mathematical model for the mass transfer from an aqueous drop to SC—$CO_2$+ethanol was developed to study the drying of aqueous solutions of lysozyme with $CO_2$+ethanol mixtures [12].

Another approach was applied using SC—$CO_2$ for drying of aqueous green tea extracts, employing a variation of the 'particles from gas-saturated solutions' (PGSS) process, using only pressurized $CO_2$ as the drying medium in a spray chamber at a mild temperature ranging from 30 to 60° C. and 20 MPa to obtain free-flowing powders, containing the intact active ingredients, such as antioxidant polyphenols. Kluge et al. [13, 14] applied the SFEE process to obtain composite nanoparticles of an anti-inflammatory drug (Ketoprofen™) and amorphous biodegradable polymer poly-lactic-co-glycolic acid (PLGA), finding that the PLGA concentration in the emulsion affected particle size and particle size distribution. A process was described for the encapsulation of lavandin essential oil in a matrix of n-octenyl succinic anhydride (OSAN)-modified starch by spraying an aqueous emulsion of the oil with SC—$CO_2$ applying a PGSS drying technique, where the emulsion was continuously mixed with $CO_2$ at 10 MPa and sprayed into a precipitation chamber at atmospheric pressure [15]. The oil was also encapsulated in polyethylene glycol (PEG) applying a PGSS technique, where the PEG was used in a molten form containing pressurized $CO_2$ forming a gas-saturated solution, which was mixed with the lavandin oil and sprayed into a precipitation chamber at atmospheric pressure [15].

The prior art does not provide any solutions regarding the formation of micro/nano-sized particles, agglomerates or fibers (micro- or nanoparticles) from water-soluble high molecular weight (HMW) biopolymers, such as HMW gums and polysaccharides with molecular weights ranging from about 70,000 g/mol (70 kDa) up to over 1,000,000 g/mol (1,000 kDa), applying a SCF drying (SFD) and/or gas antisolvent (GAS) technique. As known to those skilled in the art HMW biopolymers, in particular polysaccharides, form highly viscous solutions. This is a major challenge, which complicates the spraying and atomization process involved in SFD and GAS. For example, β-glucan (BG) with a MW up to 500 kDa can form solutions having viscosities ranging between 100 to 1,500 mPa·s at concentrations as low as about 1% (w/w) in water. Furthermore, the prior art is also silent when it comes to impregnation of such micro- or nanoparticles with bioactives or encapsulation of bioactives in micro- or nanoparticles made from such HMW biopolymers applying supercritical fluid technology for use in cosmetic, pharmaceutical, agricultural, nutraceutical or food products.

SUMMARY OF THE INVENTION

In one aspect of the invention, the SFD/GAS process described herein is surprisingly capable of processing highly viscous aqueous solutions of HMW biopolymers into dry particles, agglomerates and/or fibers.

In one aspect, the invention may comprise a method of producing micro- or nanoparticles, as defined below, from an aqueous solution of a high molecular weight biopolymer, comprising the step of spraying the aqueous solution together with a mixture of a compressible gas and a water-soluble co-solvent/antisolvent into a pressurized chamber. In one embodiment, the chamber is flushed after finishing the precipitation of particles with sufficient amounts of a compressible gas to remove any residual co-solvent/antisolvent. The compressible gas may comprise carbon dioxide, carbon dioxide and ethanol, nitrogen, or mixtures thereof. The water-soluble co-solvent/antisolvent may comprise ethanol, acetone or isopropanol, or mixtures thereof. The aqueous solution and the compressible gas/co-solvent/antisolvent may be sprayed into the pressurized chamber through a coaxial nozzle. A water-soluble organic solvent may be mixed with the aqueous solution prior to spraying the aqueous solution into the pressurized chamber.

In one embodiment, the chamber may be flushed with a second gas having a different density than the compressible gas, to remove any residual solvents.

In another aspect, the invention may comprise a method of impregnating the micro- or nanoparticles formed in a method described herein with a bioactive, comprising the steps of:
 a) solubilizing the bioactive in a suitable solvent;
 b) continuously injecting the solubilized bioactive into the pressurized chamber to cause precipitation or dispersion of the bioactive on the previously formed micro- or nanoparticles without solubilizing the previously formed micro- or nanoparticles; and
 c) flushing the chamber with sufficient amounts of a compressible gas to remove any residual solvent.

In one embodiment, the flushing gas in step (c) comprises a second gas having a lower density than the compressible gas used in claim 1, to remove residuals of solvents to render a dry product. The bioactive may comprise a material which is substantially soluble in a solvent selected from the group consisting of water, or a water-soluble organic solvent, sub- or supercritical $CO_2$, gas-expanded ethanol, or mixtures thereof, but much less soluble in mixtures of pressurized $CO_2$ and the solvent compared to its solubility at the conditions used for forming the micro- or nanoparticles.

In another aspect, the invention may comprise a method for microencapsulating a bioactive material with a biopolymer comprising the steps of:
 a) solubilizing the bioactive in a solvent comprising water or a water-soluble organic solvent, sub- or supercritical $CO_2$, a gas-expanded liquid or mixtures thereof
 b) continuously mixing the solubilized bioactive into an aqueous solution of a biopolymer to produce a mixture; and
 c) spraying the aqueous mixture of bioactive and biopolymer together with a mixture of a compressible gas and co-solvent/antisolvent into a pressurized chamber.

In one embodiment, the bioactive solvent may comprise water, ethanol, acetone or isopropanol, or mixtures thereof, and the co-solvent/antisolvent may comprise ethanol, acetone or isopropanol, or mixtures thereof. The compressible gas comprises carbon dioxide. The chamber may be flushed after finishing the precipitation of particles with sufficient amounts of the compressible gas to remove any residual solvent, or co-solvent/antisolvent. Alternatively the chamber may be flushed using a second gas having a lower density than the compressible gas used in step (c) to remove any remaining solvent, or co-solvent/antisolvent to render a dry product.

In one embodiment, the high molecular weight biopolymer in any method described or claimed herein comprises a polysaccharide. The polysaccharide may have a molecular weight of 70 kDa or more, and may comprise gum arabic or β-glucan.

In one embodiment, the bioactive may comprise any bioactive material as defined herein, and in exemplary embodiments may comprise a fish oil, plant oil or plant oil saturated with carotenoids.

In yet another aspect, the invention may comprise a product comprising micro- or nanoparticles, or agglomerates thereof, of a biopolymer having a molecular weight greater than 70 kDa, and having a bulk density of less than 0.10 g/mL. In one embodiment, the product may comprise β-glucan having a bulk density of about 0.01 g/mL, after milling to form free flowing fiber agglomerates of less than 5 mm in length. β-Glucan produced in accordance with the methods described herein is highly soluble in water, such that a 1% (w/w) aqueous solution forms in about 45 minutes at 45° C., and about 30 minutes at 55° C.

In one embodiment, the products formed by the methods described herein comprise a biopolymer having a molecular weight which is substantially similar to that of the biopolymer before processing.

BRIEF DESCRIPTION OF THE DRAWINGS

In the drawings, like elements are assigned like reference numerals. The drawings are not necessarily to scale, with the emphasis instead placed upon the principles of the present invention. Additionally, each of the embodiments depicted are but one of a number of possible arrangements utilizing the fundamental concepts of the present invention. The drawings are briefly described as follows.

DETAILED DESCRIPTION OF PREFERRED EMBODIMENTS

Figure 1:
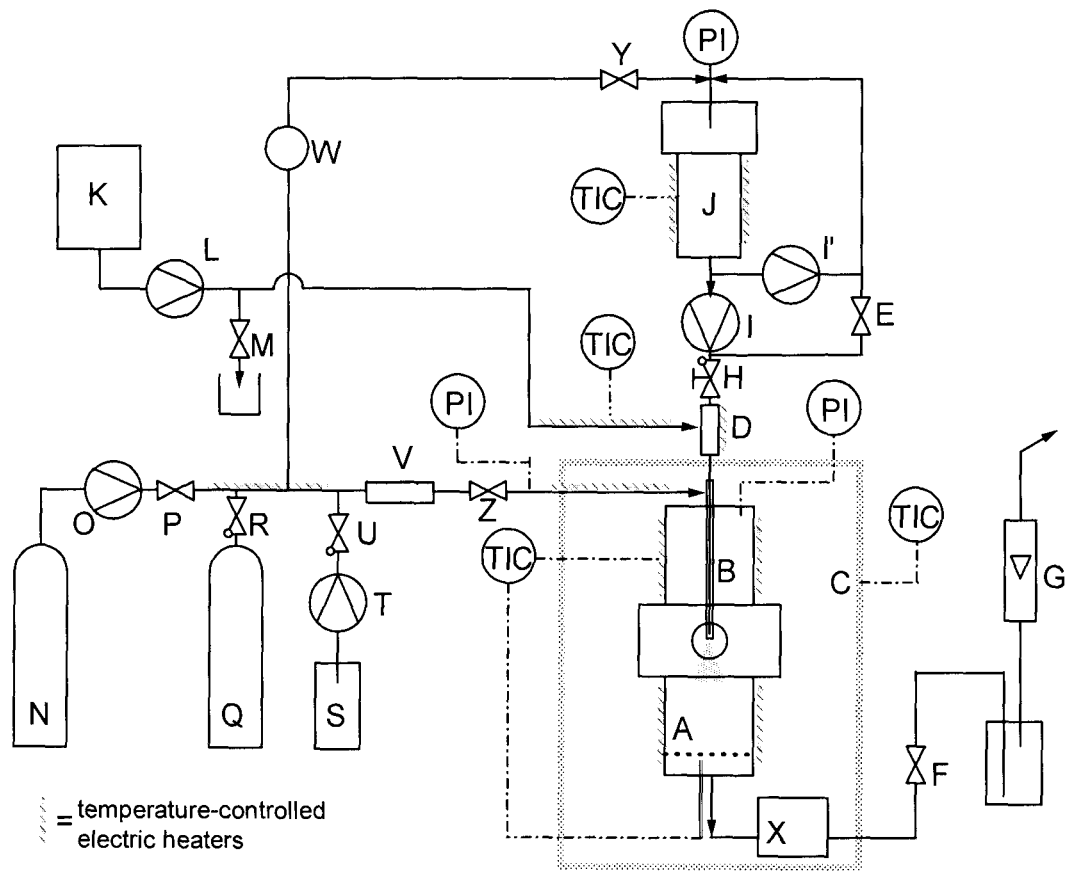
FIG. 1 shows a schematic depiction of one embodiment of an apparatus for particle formation, microencapsulation and impregnation: A) view cell equipped with filter; B) coaxial nozzle; C) thermostated circulating air bath; D) emulsifying device; E) needle valve; F) heated micrometering valve; G) rotameter; H) check valve and shut-off valve; I and I') piston pump; J) top reservoir; K) reservoir of aqueous solution; L) piston pump; M) needle valve; N) $CO_2$ cylinder; O) syringe pump; P) shut-off valve; Q) $N_2$ cylinder; R) shut off valve; S) reservoir of ethanol; T) HPLC pump; U) check valve; V) static mixer; W) pressure regulator; X) UV/VIS cell; Y, Z) shut-off valve. (Abbreviations: PI—pressure indicator; TIC—temperature indicator and controller.)

The invention relates to methods of producing novel microparticles and nanoparticles comprising high molecular weight biopolymers, which may or may not comprise added bioactive material. When describing the present invention, all terms not defined herein have their common art-recognized meanings. To the extent that the following description is of a specific embodiment or a particular use of the invention, it is intended to be illustrative only, and not limiting of the claimed invention.

As used herein, the term "micro- or nanoparticles" means any particles, agglomerates, fibers, fibrils, spheres, globules or other three-dimensional conformations of a biopolymer, which have a dimension in the microscale in the case of microparticles, or in the nanoscale in the case of nanoparticles. In one embodiment, microparticles are particles which have a dimension between about 1000 nm and 100 micrometers, and nanoparticles are particles which have a dimension less than about 1000 nm, preferably less than about 100 nm. In one embodiment, the microparticles or nanoparticles may have a spherical, elongated or some other regular or irregular shape.

As used herein, high molecular weight biopolymers are comprised of molecules having molecular weights ranging from about 70,000 g/mol to over 1,000,000 g/mol (i.e. 70 to 1,000 kDa), which are polymers produced by living organisms or are of biological origin, and which are substantially water soluble. Exemplary biopolymers include, without limitation, gums and polysaccharides, such as gum arabic (which also includes glycoproteins) or β-glucan.

The term "bioactive" refers to any substance that interacts with any cell tissue in the human or animal body, or which interacts with prokaryotic or eukaryotic cells. Bioactive material may include pharmaceutical or nutraceutical substances, anti-inflammatory, antimicrobial, antiviral or antifungal substances, or material generally believed to have a beneficial effect on health or well-being. In one embodiment, suitable bioactive material for use with the present invention includes material, which is substantially soluble in water, ethanol, aqueous ethanol, water-soluble organic solvents or gas-expanded solvents, such as $CO_2$-expanded ethanol or mixtures thereof, and may include lipid-based material such as fish oil or vegetable or other specialty oils, or other lipids comprising mono- or polyunsaturated fatty acids or lipid-soluble bioactives such as carotenoids, phytosterols, or tocopherols, as well as polyphenols, terpenoids, antioxidants, peptides, proteins, or any other substance, which may exhibit beneficial health effects and that could be used to impregnate the formed particles, agglomerates or fibers. The bioactive may be soluble in water, or water-soluble solvents, but may precipitate when processed with the supercritical fluid drying/gas antisolvent processes.

The present invention is directed to methods of producing micro- and nanoparticles from high molecular weight biopolymers using supercritical fluid technology. It is further directed to methods of microencapsulating or impregnating bioactive materials into agglomerates or onto the micro- or nanoparticles. The micro- and nanoparticles generally have a large surface area, low bulk density and may be highly porous. These properties may facilitate easier handling and dispersion, and dissolution in water that is much faster than powders of the same biopolymers prepared by prior art techniques.

In one aspect, the invention relates to a process combining supercritical fluid drying technique with a gas antisolvent technique (SFD/GAS) for particle formation from aqueous solutions containing HMW biopolymers.

In one embodiment, the invention comprises a method of producing micro- or nanoparticles comprising the steps of spraying the aqueous solution of biopolymers into a pressurized chamber through a coaxial nozzle together with a mixture of a pressurized gas and a co-solvent/antisolvent. The pressurized gas may comprise carbon dioxide, and the co-solvent/antisolvent may comprise a water-soluble organic solvent, such as ethanol, acetone, or isopropanol. In one embodiment, it may be preferred to inject the co-solvent/antisolvent into the aqueous biopolymer solution prior to spraying, to generate nanoparticle agglomerates. As used herein, the term "coaxial nozzle" means any nozzle having a coaxial configuration. As are known in the art, coaxial nozzles typically have at least two passages which share a common axis and terminate adjacent one other at an outlet end, with each passage carrying the flow of a specific material.

In one embodiment, the HMW biopolymers may comprise polysaccharides such as gum arabic (GA) or β-glucan (BG). In one embodiment, the SFD/GAS process may take place at mild temperature conditions ranging from 25 to 80° C. and elevated pressure ranging from 8 to 40 MPa. The solvent may comprise a water-soluble organic co-solvent, for example, without limitation, such solvents as ethanol, acetone, or isopropanol, or mixtures thereof, at concentrations ranging from 20 to 80% (w/w) in sub- or supercritical $CO_2$. The solvent functions as a co-solvent to enhance water solubility in $CO_2$ and as an antisolvent to precipitate the HMW biopolymers.

The morphology of the obtained HMW biopolymer precipitate from the SFD/GAS process depends substantially on the nature of the biopolymer. For example, the precipitate of BG is different from that of GA obtained by the SFD/GAS process using ethanol as co-solvent/antisolvent. While GA forms micro/nano-sized spherical and amorphous particles and agglomerates of nanoparticles, BG forms fibrils and highly porous sheet-like structures with a large surface area resembling a cob-web structure comprised of fibrils with a thickness ranging from under 100 nanometer to about 1 micrometer. The bulk density of the micro- and nanoparticles of GA may be less than about 0.10 g/mL, and may be less than about 0.05 g/mL, for example between about 0.017 and about 0.042 g/mL. The bulk density of the micro- and nanoparticles of BG is even lower, and may be less than about 0.050 g/mL, and may be less than about 0.010 g/mL, for example about 0.005 g/mL. These bulk densities are similar to that of aerogels of GA or BG produced by other methods.

In another embodiment of the invention, agglomerates of nanoparticles may be formed by a process comprising the steps of:

(a) continuously injecting a co-solvent/antisolvent into the aqueous solution of the biopolymer to form a mixture; and (b) continuously spraying the mixture together with a drying fluid through a coaxial nozzle into a precipitation chamber.

The co-solvent/antisolvent may comprise a water-soluble organic solvent, such as ethanol, acetone, or isopropanol, or mixtures thereof, and the drying fluid may comprise pressurized carbon dioxide and the same co-solvent/antisolvent. Due to the higher initial load of antisolvent in the aqueous biopolymer solution, precipitation of the particles is initiated before atomization and leads to faster precipitation of biopolymers once the solution is contacted with the $CO_2$+co-solvent/antisolvent mixture in the coaxial nozzle. Without restriction to a theory, the fast precipitation may be caused by the antisolvent lowering the dielectric constant of the aqueous solution. The result is that smaller sized nanoparticles are formed, which then may agglomerate into larger clusters.

The micro- and nanoparticles are mostly of spherical morphology and have a diameter typically ranging from less than 100 nanometer up to 1 micrometer. The particles may form agglomerates having a mean particle size ranging from about 10 micrometers to 40 micrometers.

The process may be adapted to comprise a method for impregnation of a bioactive onto micro- or nanoparticles of the HMW biopolymer formed by the SFD/GAS process. The impregnated micro- and nanoparticles may thus be used as a carrier for the bioactive, for example, as a delivery system in pharmaceutical, cosmetic, agricultural, nutraceutical or food applications.

In general terms, an aqueous solution of biopolymers may be sprayed into a pressurized chamber through a coaxial nozzle together with a mixture of a pressurized gas and a co-solvent/antisolvent (comprising of a water-soluble organic solvent, such as ethanol, acetone, or isopropanol, or mixtures thereof). In one alternative, the co-solvent/antisolvent may be injected into the aqueous biopolymer solution prior to spraying, which facilitates formation of agglomerates of the micro- or nanoparticles. The bioactive may then be impregnated onto the micro- or nanoparticles by spraying a solution, dispersion, or emulsion containing the bioactive onto the particles at different processing conditions (i.e. pressure, temperature), and/or employing another fluid mixture for atomization in the coaxial nozzle than those used during particle precipitation to avoid extraction of the bioactive. The atomizing fluid can be comprised of pressurized $CO_2$, nitrogen, air, ethanol, water, any compressible or liquefied gas, sub- and supercritical fluids or mixtures thereof in order to avoid solubilisation/extraction of the bioactive from the matrix of micro- or nanoparticles during impregnation.

Alternatively, the impregnation step may take place directly after formation of the micro- or nanoparticles by introducing a fluid mixture carrying the bioactive and by changing the processing conditions (i.e. pressure, temperature), thereby changing solubility in the fluid to cause precipitation of the bioactive onto the micro- or nano particles. Alternatively, other known supercritical fluid techniques for impregnation of carriers known to those skilled in the art may be used. The bioactive may be dissolved or dispersed in an appropriate solvent (i.e. sub- or supercritical $CO_2$, nitrogen, organic solvents, ethanol, water, lipids, other compressible or liquefied gases or sub- and supercritical fluids or mixtures thereof) and sprayed onto the particles, thereby applying the bioactive under appropriate processing conditions to avoid collapsing of the fibers due to interfacial tension, capillary action or other effects.

If the bioactive exhibits pronounced solubility in pressurized $CO_2$, or a co-solvent/antisolvent (such as a water-soluble organic solvent, for example, ethanol, acetone, or isopropanol, or mixtures thereof) under the conditions required for encapsulation/precipitation during the SFD/GAS process, it would lead to extraction and depletion of the bioactive from the micro- or nanoparticles during SFD/GAS processing. Therefore, the SFD/GAS process leading to the formation of the micro- or nanoparticles may be followed by an impregnation step, which may comprise spraying a solution/dispersion or emulsion of the bioactive onto the micro- or nanoparticles using different processing conditions (pressure, temperature), and/or using another fluid mixture for atomization in the coaxial nozzle than those used for particle precipitation. In that manner, extraction of the bioactive may be avoided.

The atomizing fluid can be comprised of pressurized $CO_2$, nitrogen, air, ethanol, water, any compressible or liquefied gases, sub- and supercritical fluids or mixtures thereof in order to avoid solubilization of the bioactive during impregnation. In order to atomize or disperse the bioactive in the coaxial nozzle, it may be first be dissolved in a suitable solvent, which may comprise of water, pressurized $CO_2$, an organic solvent, lipids, or mixtures thereof, prior to the spraying and impregnation step either in a separate processing step or by means of a continuous injection process.

In another embodiment, a solution, dispersion or emulsion of the bioactive may be sprayed onto micro- or nanoparticles formed by the SFD/GAS process. Preferably the micro- or nanoparticles may be fluidized to form a fluidized bed, applying known techniques of the art and then the bioactive may be sprayed onto the particles, facilitating an even distribution.

In another embodiment, the process may be adapted to microencapsulate a bioactive, with the HMW biopolymer forming a shell around the bioactive. In one embodiment, and in general terms, a solution/dispersion or emulsion of the bioactive in an aqueous solution of the HMW biopolymer is prepared either by using methods known to those skilled in the art, or by a continuous injection process. The mixture is then sprayed into a pressurized chamber together with a mixture of the drying fluid, which may be comprised of pressurized $CO_2$ and ethanol, using a coaxial nozzle.

The term "microcapsules" means particles comprised of a high molecular weight biopolymer and a bioactive material, which may or may not be entirely enclosed by arrangements of the biopolymer particles. The particles may comprise spheres or other regular or irregular shapes, and may range in size such that the microcapsule has at least one dimension less than about 1 mm, and preferably less than about 500 µm, and more preferably less than about 100 µm.

In one embodiment, the bioactive is solubilized in a suitable solvent, which may comprise water, a water-soluble organic solvent, such as ethanol, acetone, or isopropanol, lipids, or a gas-expanded solvent or mixtures thereof. The solubilized bioactive is then injected into an aqueous solution of the shell material to produce a mixture, causing dissolution of the solvent into the aqueous phase leading to initiation of shell formation. Without restriction to a theory, it is believed that the solvent lowers the dielectric constant in the aqueous solution causing initiation of shell formation, and the bioactive is finely dispersed due to stranding. The mixture is then injected into a pressurized chamber together with a mixture of a pressurized gas and a co-solvent/antisolvent to form the microcapsular shell material and bioactive material.

The bioactive material may be soluble in water, water-soluble organic solvents, such as ethanol, acetone, or isopropanol, or lipids to facilitate preparation of a dispersion or emulsion with the HMW biopolymer solution, but insoluble or less soluble in either $CO_2$, a co-solvent/antisolvent comprising of water-soluble organic solvents, such as ethanol, acetone, or isopropanol, or mixtures thereof, at the processing conditions of the SFD/GAS process. Accordingly, when the aqueous solution/dispersion or emulsion of the HMW biopolymer carrying the bioactive is being sprayed into the pressurized chamber applying the SFD/GAS process, the bioactive may co-precipitate with the HMW biopolymer and thus be encapsulated by agglomerates of the precipitating micro- or nanoparticles, or be impregnated into the particles.

It is known that pressurized carbon dioxide can act as a biocide leading to inactivation of bacteria, molds, fungi and spores [16, 17]. In one embodiment, the conditions used in the SFD/GAS process employing pressurized carbon dioxide and high concentrations of ethanol thus facilitate the sterility of the product by destroying or inactivating potential microorganisms present in the starting material, so that powders or fibers produced by this SFD/GAS process are essentially sterile, thereby reducing the need for preservatives in the final dry product.

The micro- and nanoparticles resulting from the methods described above have properties which distinguish them from the prior art. For example, BG particles produced by the methods described herein typically take the form of fibers, and have significantly lower bulk density and markedly better solubilization than prior art BG products. Without restriction to a theory, it is believed that the three dimensional structure and the large surface area which results from very fine porous morphology of the fibers, facilitates dissolution into water. The structure of the microfibrils helps to prevent the BG fibers from clumping when added into water. Furthermore, the low bulk density of the microfibrils, which is about 0.01 g/mL, facilitates fine dispersion of the fibrous particles when added into water, keeping the fibrous strands better separated when contacted with water than powderous material. The fibrous, porous structure and morphology of the microfibers lead to a behavior similar to a sponge facilitating uptake of water to evenly wet the fibers and preventing clumping due to capillary action.

Therefore, the microfibers produced by the SFD/GAS method consisting of oat or barley β-glucan with a high molecular weight dissolve much faster in water than other BG powders currently commercially available.

EXAMPLES

The following examples are provided to exemplify aspects of the present invention described herein, and not to limit the claimed invention in any way. The following examples investigate the effects of various process parameters, such as nozzle design, flow rate, solids concentration, and pressure on particle morphology, particle size distribution and finally oil content in fish oil microcapsules, produced in accordance with embodiments of the invention.

Example 1

Materials

Gum arabic (GA) was used as purchased without any further treatment (ACROS Organic, Fisher Scientific, Canada). β-Glucan (BG) powder (moisture content of 8.7% and BG content of 75% dry weight basis) previously extracted from barley in our lab according to the protocols described by Ghotra et al. [18] was used in the different experiments. Refined fish oil extracted from anchovy and sardine was obtained from Ocean Nutrition Canada (ONC, Halifax, NS, Canada) with a level of 8 and 25% for eicosapentaenoic acid (EPA) and docosahexaenoic acid (DHA), respectively. Food grade anhydrous ethanol (Commercial Alcohol, Winnipeg, MB, Canada) with a stated purity and water content of 99.99% and 0.008% by volume, respectively, was used without further purification. Hexane of analytical grade (Fisher Scientific, Canada) was used for determining the lipid content of fish oil microcapsules. Bone dry $CO_2$ with a purity of 99.9% and nitrogen with a purity of 99.998% were purchased from Praxair (Edmonton, AB, Canada). For impregnation experiments, canola oil saturated with carotenoids was prepared by extraction from carrots according to the optimized conditions described by Sun and Temelli [19].

Example 2

Apparatus

The apparatus used for micro- or nanoparticle formation, microencapsulation and impregnation consisted of a 200 mL view cell with an internal diameter of 40 mm (Nova-Swiss, Effretikon, Switzerland) equipped with a coaxial-nozzle, temperature-controlled heaters and circulating air bath, shown schematically in FIG. 1. The system was pressurized with $CO_2$ by means of a syringe pump (O) (Isco Model 260D, Isco Inc., Lincoln, Nebr.). $CO_2$ was preheated to 45° C. using temperature-controlled electric heaters and mixed with ethanol, which was pumped into the system with an HPLC pump (T) (Gilson 305, HPLC pump, Gilson Inc., Middleton, Wis.).

The mixture of $CO_2$+ethanol passed through a double-helix static mixer prior to injection into the view cell flowing in the outer channel of the coaxial nozzle (B). The flow rate of $CO_2$ was adjusted using a heated metering valve (F) at the outlet of the view cell, and monitored by means of a rotameter (G), which was located after a sealed collection bottle trapping ethanol. The flow rate of $CO_2$ delivered into the system was displayed by the ISCO syringe pump controllers which were set to constant pressure mode.

Figure 2:
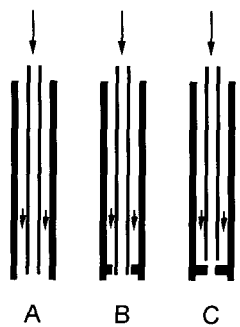
FIG. 2 shows three coaxial nozzle configurations (A, B and C) tested in the supercritical drying process.

An aqueous solution containing the biopolymers to be precipitated was pumped by means of a metering piston pump (L) (LEWA GmbH, Leonberg, Germany) into the inner tube of the coaxial nozzle and sprayed into the view cell (A). Due to the high viscosity of the aqueous solutions containing HMW biopolymers, such as BG, the metering piston pump was equipped with additional spring-loaded poppet check valves (Swagelok Inc., Edmonton, AB) at the inlet and outlet of the pump. Three different arrangements were tested for the coaxial nozzle consisting of two seamless stainless steel tubings, and optionally a cap with an orifice or orifice insert installed at the nozzle tip, as illustrated in FIG. 2.

The outer tubing of the coaxial nozzle had an OD and ID of 6.35 and 3.05 mm, while those of the inner tubing were 1.59 and 1.08 mm, respectively. Modified set-screw style threaded orifice inserts (ZM-35-M4-5-SS, O'Keefe Controls, Trumbull, Conn.) were fitted into the outer tubing at the nozzle tip (nozzles B and C). The orifice diameter for nozzle B was 1.75 mm, while for nozzle C two orifice diameters, namely 0.51 and 0.89 mm, were tested. For design C, the orifice length and the gap between the tip of the inner tubing and the nozzle orifice were both about 1 mm. The jet emerging from the nozzle tip could be observed through the window in the middle of the view cell allowing the observation of jet breakup, atomization, particle precipitation and nozzle clogging. The distance from the nozzle tip to the filter plate at the bottom of the view cell was about 7 cm. The filter to collect the particles consisted of a sintered metal frit with pore size of 10 μm, which was covered with a 0.1 μm nylon filter for each experiment to collect the particles.

Figure 3:
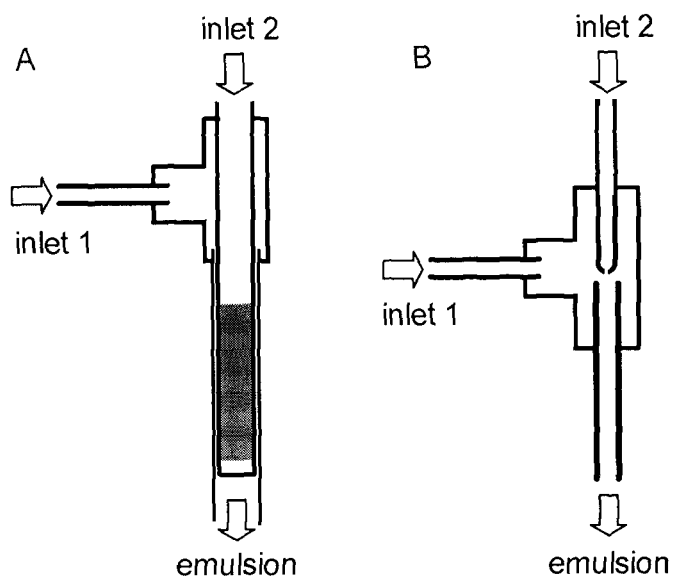
FIGS. 3A and 3B show two types of emulsifying device used to continuously inject fish oil and/or solution containing the bioactive into the aqueous solution of shell matrix.

In order to continuously generate an emulsion of fish oil in the aqueous solution, two different emulsifying devices (EMD) were assembled, as illustrated in FIG. 3.

For all experiments the aqueous solution with the shell material was pumped into inlet 1 of the EMD. As well, in case of the microencapsulation experiments, a mixture of fish oil+$CO_2$-expanded ethanol (CX EtOH) was injected through inlet 2 of the EMD (FIG. 3) to disperse the oil in the aqueous solution. The first design (FIG. 3A) consisted of a sintered stainless steel sparging element (Mott Corp., Farmington, Conn.) with an OD of 6.35 mm and average pore size ranging from 0.2 to 5 μm placed inside a stainless steel tubing with an ID of 7.04 mm, thereby leaving only a very narrow annulus between the sparger element and housing tube in order to generate high shear rates facilitating membrane emulsification. The second design (FIG. 3B), consisted of a stainless steel union-Tee (Swagelok Inc., Edmonton, AB) with a custom-made nozzle having a round cap and orifice diameter of 50 μm (Lenox Laser Inc., Glen Arm, Md.) pointing at the entrance of the outlet tube (OD and ID of 6.35 and 2 mm, respectively), leaving only a narrow gap between the nozzle tip and the outlet tube (0.5 mm) to generate high shear rates at the point of oil injection to facilitate emulsification.

For the microencapsulation experiments, the top reservoir of the apparatus was used to prepare a mixture of fish oil+CX EtOH. The top reservoir (60 mL) connected to a dual head piston pump (Minipump, Milton Roy, Ivyland, Pa.), where one pump head was used to circulate the fish oil+CX EtOH mixture at a flow rate of 9.2 mL/min from the bottom to the top of the reservoir to facilitate equilibration, while the other pump head set to a flow rate ranging from 0.4 to 0.8 mL/min was used to inject that fish oil mixture into the emulsifying device at inlet 2 (FIG. 3). Since the performance of the check valves of that pump was found to be unpredictable at elevated pressures, additional external spring loaded check valves (Swagelok Inc., Edmonton, AB) were installed at the pump head used to inject the fish oil mixture into the EMD. A high pressure UV/VIS detector (X) (Milton Roy, Ivyland, Pa.) set to a wavelength of 290 nm was used at the outlet of the view cell to monitor the concentration of ethanol in the outlet stream of the view cell, allowing to observe in situ when steady state was reached.

Example 3

Dry Particle Formation

Formation of micro- or nanoparticles, microencapsulation and impregnation experiments were carried out with the view cell preheated to 40° C., while the $CO_2$+EtOH mixture was preheated to 45° C. in the tubing leading to the nozzle. The slightly higher temperature in the pre-heater was chosen to compensate for the cooling due to the Joule-Thomson effect during the expansion in the nozzle. The temperature in the spray chamber decreased during spraying from 40° C. to a constant value of about 38° C. For the particle formation experiments, various process parameters and conditions were evaluated during preliminary tests, including pressure, flow rates, nozzle setup, emulsifying device setup and concentration of solids in the aqueous solution as listed in Table 1. An overview of the experimental conditions studied is provided in Table 2.

In order to prepare dry nano-agglomerate particles from an aqueous solution containing 10% (w/w) GA, the GA solution was pumped at a flow rate of 2 mL/min and mixed with absolute ethanol at a flow rate of 4 mL/min using the emulsifying device with the nozzle setup (FIG. 3B) prior to spraying. This presaturated solution of GA in aqueous ethanol was continuously sprayed into the precipitation chamber at 10 MPa and 40° C. using the coaxial nozzle together with pressurized $CO_2$ at a flow rate of 25 mL/min which was premixed with absolute ethanol at a flow rate of either 16 or 20 mL/min.

TABLE 1

List of parameters tested for particle formation and microencapsulation.

| Process parameter | Range | Unit |
| --- | --- | --- |
| Temperature | 40 | ° C. |
| Pressure | 24 | MPa |
|  | 10 | MPa |
| Nozzle setup | A, B, C |  |
| Orifice diameter | 0.89 | mm |
|  | 0.51 | mm |
| $CO_2$ flow rate | 21 | mL/min |
|  | 25 | mL/min |
|  | 32 | mL/min |
| EtOH flow rate | 12 | mL/min |
|  | 24 | mL/min |
| Flow rate of aqueous solution | 0.45 | mL/min |
|  | 0.9 | mL/min |
|  | 1.9 | mL/min |
|  | 2.8 | mL/min |
| Solid concentration[#] BG (wt %, as is basis) | 0.84 | wt % |
|  | 0.95 | wt % |
|  | 1.67 | wt % |
| GA | 21.8 | wt % |
|  | 10 | wt % |
| GA + BG | 10 + 0.5 | wt % |
| Emulsifying device setup | FRIT NOZZLE |  |

[#]GA: gum arabic, BG: β-glucan.

TABLE 2

Experimental conditions for particle formation and encapsulation.

| Experiment[#] | P [MPa] | Flow rate [mL/min] | | | | Spray solution | | | Emulsifier setup[$] |
|---|---|---|---|---|---|---|---|---|---|
| | | Fish oil | $CO_2$ | EtOH | Solution | Solute | [wt %] | [mL] | |
| GA_1 | 24 | | 25 | 24 | 0.45 | GA | 10 | 5 | FRIT |
| GA_2 | 24 | | 25 | 24 | 0.45 | GA | 10 | 4.5 | FRIT |
| GA_3 | 24 | | 25 | 23 | 12 | 0.45 | GA | 10 | 5 FRIT |
| BG_1 | 24 | | 25 | 24 | 0.73 | BG | 0.84 | 4.5 | no FRIT/cap |
| BG_2 | 24 | | 25 | 24 | 0.785 | BG | 0.84 | 21.5 | no FRIT/cap |
| BG_3 | 24 | | 25 | 24 | 0.73 | BG | 1.67 | 18 | no FRIT/cap |
| GA_BG_1 | 24 | | 25 | 24 | | GA | 10 | 5 | no FRIT/cap |
| | | | | | | BG | 0.5 | 5 | |
| GA_BG_2 | 24 | | 25 | 24 | 1.9 | GA | 9.8 | 1.5 | no FRIT/cap |
| | | | | | | BG | 0.5 | 1.5 | |
| GA_BG_3 | 24 | | 25 | 24 | 1.9 | GA | 9.93 | 7 | NOZZLE |
| | | | | | | BG | 0.5 | 7 | |
| GA_BG_4 | 10 | | 25 | 24 | 1.88 | GA | 9.87 | 7.5 | NOZZLE |
| | | | | | | BG | 0.52 | 7.5 | |
| GA_BG_FO_1 | 24 | 0.3 | 25 | 24 | 1.9 | GA | 9.93 | 8.5 | NOZZLE |
| | | | | | | BG | 0.5 | 8.5 | |
| GA_BG_FO_2 | 10 | 0.3 | 25 | 24 | 1.88 | GA | 9.87 | 7 | NOZZLE |
| | | | | | | BG | 0.52 | 7 | |
| GA_BG_FO_3 | 10 | 0.8 | 25 | 24 | 1.42 | GA | 9.87 | 10 | NOZZLE |
| | | | | | | BG | 0.52 | 10 | |

[#]GA: gum arabic; BG: β-glucan; FO: fish oil.
[$]FRIT: EMD type A; no FRIT/cap: replaced sparging element with a cap: NOZZLE: EMD type B.

For the particle formation experiments, the system was heated to 40° C. and pressurized with $CO_2$ to the experimental pressure. A continuous flow rate of $CO_2$ was established by adjusting the heated metering valve at the outlet of the view cell. The co-solvent pump (T) was started to continuously deliver EtOH to the system at the desired flow rate. After about 10 min, steady state was reached as evidenced by the constant absorption indicated by the UV/VIS detector, as well as a constant temperature in the view cell. The spray process was started by switching on pump (L) delivering the aqueous solution of HMW biopolymer into the coaxial nozzle.

Spraying of the aqueous solution could be observed through the window of the view cell so that if clogging of the nozzle occurred, a pressure impulse was generated by closing the shut-off valve (Z) at the inlet of the nozzle for a few seconds so that the flow of the incoming $CO_2$+EtOH mixture could be interrupted and a pressure pulse was generated, which generally freed the nozzle orifice from a plug. Spraying of the aqueous solution was carried out for about 5 to 10 min until the spray chamber seemed to be full of particles, which were swirling around inside the spray chamber. However, due to fine particles depositing in the cavity of the window of the cell the view of the nozzle was blocked after several minutes. Using the pressure indicators installed before and after the nozzle the occurrence of blocking in the nozzle could be detected by monitoring the pressure drop across the nozzle.

At the end of the experiment, the tubing between the nozzle and pump (L) was back-flushed carefully by opening the needle valve (M) so that the remaining aqueous solution was pushed out of the line, to avoid drops from falling out of the nozzle onto the dried particles during the depressurization step. After the spraying was stopped, the ethanol pump was stopped and the view cell was flushed with pure $CO_2$ at the same pressure and temperature conditions until no more ethanol was collected in the collection flask at the outlet of the view cell. Then the $CO_2$ inlet valve (P) was closed and the valve of the nitrogen cylinder (R) opened, which gradually led to a change of pressure inside of the view cell to that of the pressure level of the nitrogen cylinder, which was about 16 MPa. Then, pressurized nitrogen was flushed through the view cell until all $CO_2$ was replaced, as monitored by the UV/VIS detector. Thereby, no liquid $CO_2$ was formed inside the view cell and all remaining ethanol potentially dissolved in $CO_2$ was pushed out of the cell, prior to depressurization. As soon as all $CO_2$ was removed from the cell, the view cell was depressurized slowly to atmospheric pressure and particles precipitated onto the filter paper inside the view cell were collected.

Example 4

Impregnation of Particles with a Bioactive

Impregnation of nanoparticle agglomerates precipitated from an aqueous solution of GA presaturated with ethanol as described above was carried out after the particle precipitation process in the same chamber. After the precipitation and drying, the chamber containing the particles was flushed with pressurized $CO_2$ at 10 MPa to remove residual ethanol. Once no more ethanol was collected at the outlet of the vessel, canola oil saturated with carotenoids (CO) was injected at a flow rate of about 0.05 mL/min together with pressurized $CO_2$ at a flow rate of 40 mL/min at 10 MPa and 40° C., thereby causing the particles to be fluidized inside the chamber and the carotenoid-rich oil to be finely dispersed onto the particles. Atomization of CO was facilitated by pressurized $CO_2$, which leads to a decrease in interfacial tension between canola oil and $CO_2$ at elevated pressures and thus aids in fine droplet formation. The total amount of carotenoid-rich oil sprayed onto the particles was about 20% of the mass of particles present in the precipitation chamber. Instead of $CO_2$, it may be possible to use pressurized nitrogen for the impregnation step in order to fluidize the particles and atomize the oil in the coaxial nozzle.

Example 5

Microencapsulation of a Bioactive

Microencapsulation experiments were carried out similar to the particle formation/drying experiments, except that prior to the experiments 5 mL of fish oil and 20 mL of EtOH were filled into the top reservoir, which was preheated to 40° C. The top reservoir was then pressurized to 9 MPa with $CO_2$ addition using the pressure regulator (W). The valve (Y) was closed and the circulation pump (I and I') set to a flow rate of 18 mL/min was started, while valve (E) was open, to achieve equilibration of the EtOH+fish oil+$CO_2$ mixture. The circulation was started about 40 min prior to starting the particle formation experiments, as described in Example 3. In the microencapsulation process, the injection of aqueous solution of HMW biopolymer into the high pressure precipitation chamber together with pressurized $CO_2$+ethanol was started first and then as soon as the first solids precipitated in the view cell, the oil injection was initiated by opening valve (H) and closing valve (E), after the pump head (I) was set to the desired flow rate. The flow rates of aqueous solution and fish oil+ethanol+$CO_2$ mixture were chosen to result in a theoretical oil load in the particles of about 15-20% by weight. Similar to the particle formation protocols, the spraying was carried out until the view cell seemed to be filled with particles, which usually amounted to about 1 g of solids, at which moment the oil injection from the top reservoir was interrupted by closing valve (H) and stopping the pump (I and I') immediately. At the same time, the injection of aqueous solution was stopped by switching off pump (L). As soon as spraying was finished the ethanol co-solvent pump was stopped and the particle formation protocol was followed to depressurize and collect the dry powder.

Example 6

Characterization of Particles Obtained in Examples 3-5

Particle size and morphology were evaluated using scanning electron microscopy (SEM). For this purpose, the particles were placed on an adhesive sample stub and coated with a thin conductive layer (150 Å) of gold using a Nanotek SEMprep II sputter coater (Prestwich, Manchester, UK). The samples were analyzed with a SEM equipped with a Bruker Silicon Drift (BSD) detector and $LaB_6$ crystal source capable of providing images from 20× to 100,000× with a resolution of about 5 to 10 nm (Zeiss EVO MA 15, Carl Zeiss, Oberkochen, Germany).

Particle size distribution for the dry powder was determined in triplicate for each sample using a laser diffraction particle size analyzer (CILAS 1180, Cilas, Orleans, France) with a measurement range from 0.04 to 2500 μm. The particle size distribution for the GA nano-agglomerates was carried out using a laser diffraction particle size analyzer equipped with a tornado dry powder dispersing vacuum sampling system (Beckman Coulter, 13 320 Series Laser Diffraction Particle Size Analyzer, Beckman Coulter Inc., Brea, Calif.).

The approximate bulk density was estimated by weighing the particles directly after collecting them from the view cell and by determining their volume in a graduated cylinder.

In order to determine the lipid content in the microcapsules, the powder was dissolved in 20 mL of water at 75° C. and then thoroughly mixed with 40 mL of hexane in a separation funnel. The organic phase containing hexane and fish oil was transferred into a beaker and hexane was evaporated under the fume hood using a hot air blower at about 50° C. The remaining fish oil was determined gravimetrically.

An overview of the results obtained for various experimental conditions, such as visual appearance, bulk density, mass of powder collected and index to the SEM images for particle morphology is presented in Table 3.

TABLE 3

Summary of experimental outcomes for particle formation and encapsulation.

Figure 7:
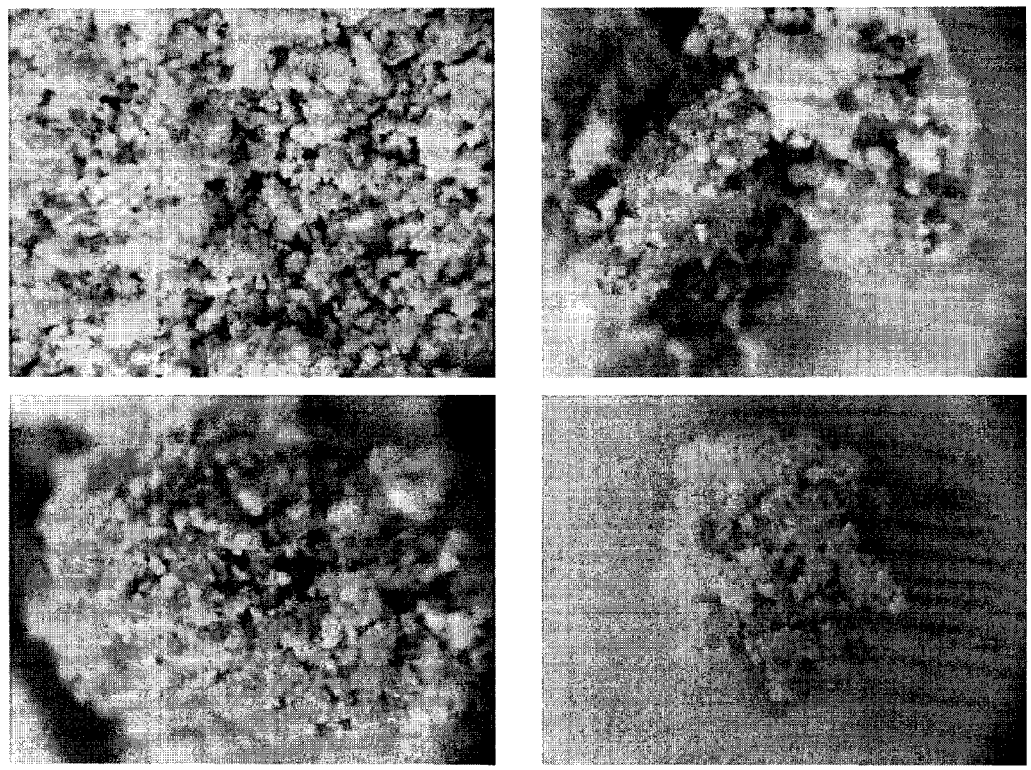
FIG. 7 shows GA particles impregnated with canola oil rich in carotenoids.
Figure 8:
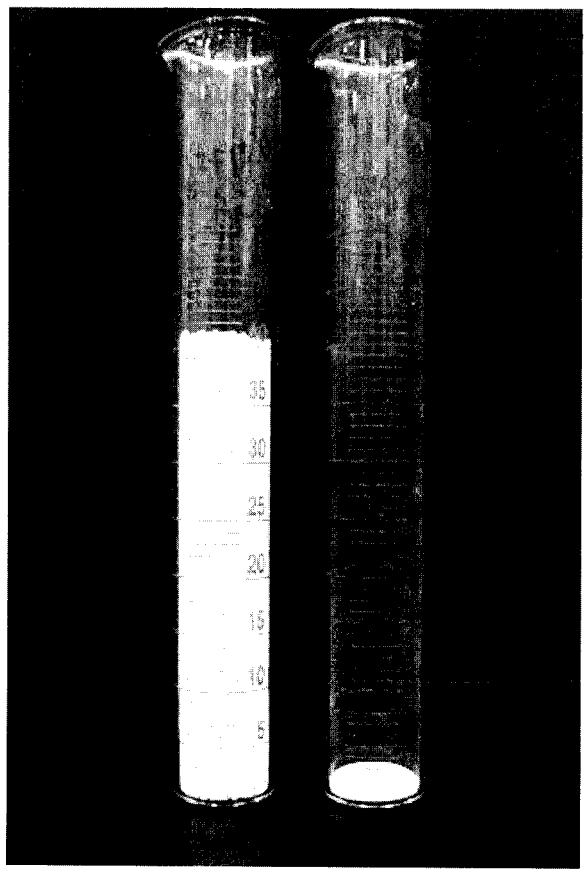
FIG. 8 shows 0.8175 g of GA powder before (right) and after (left) processing with the SFD/GAS process and the substantial increase in volume.
Figure 9:
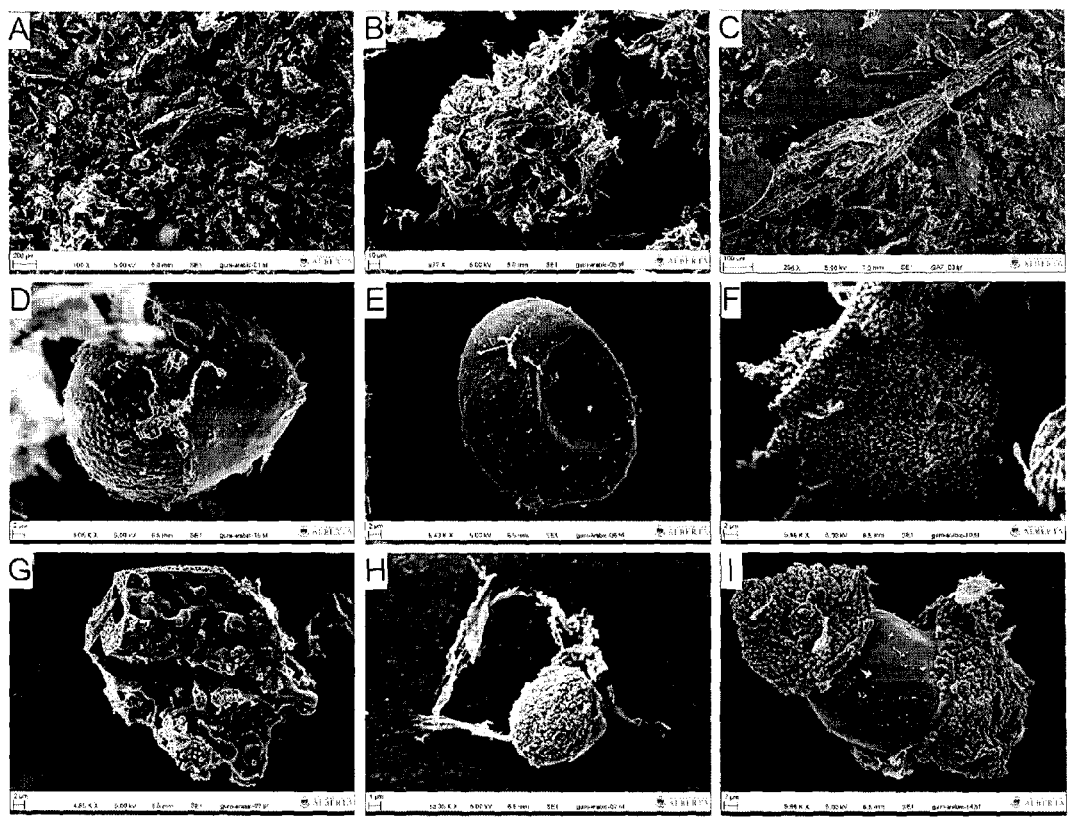
FIG. 9 shows morphologies of gum arabic (GA) particles obtained by SFD/GAS process.
Figure 10:
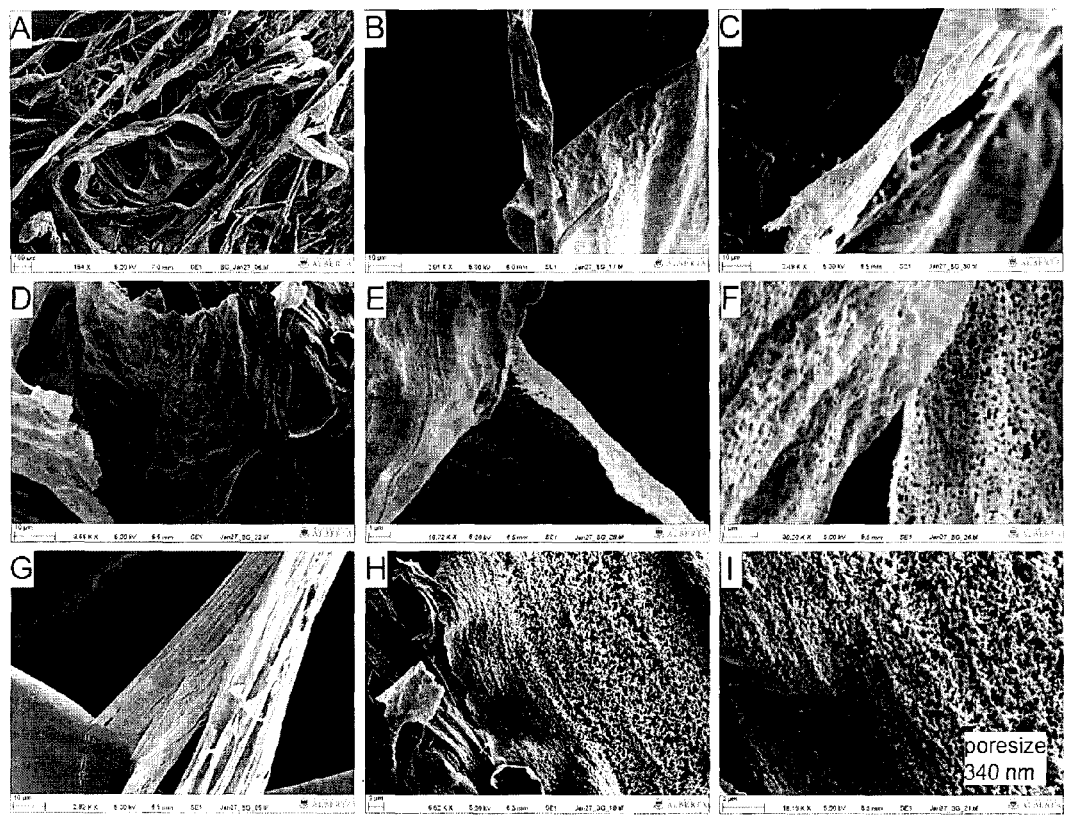
FIG. 10 shows morphologies of β-glucan (BG) particles obtained by SFD/GAS process.
Figure 11:
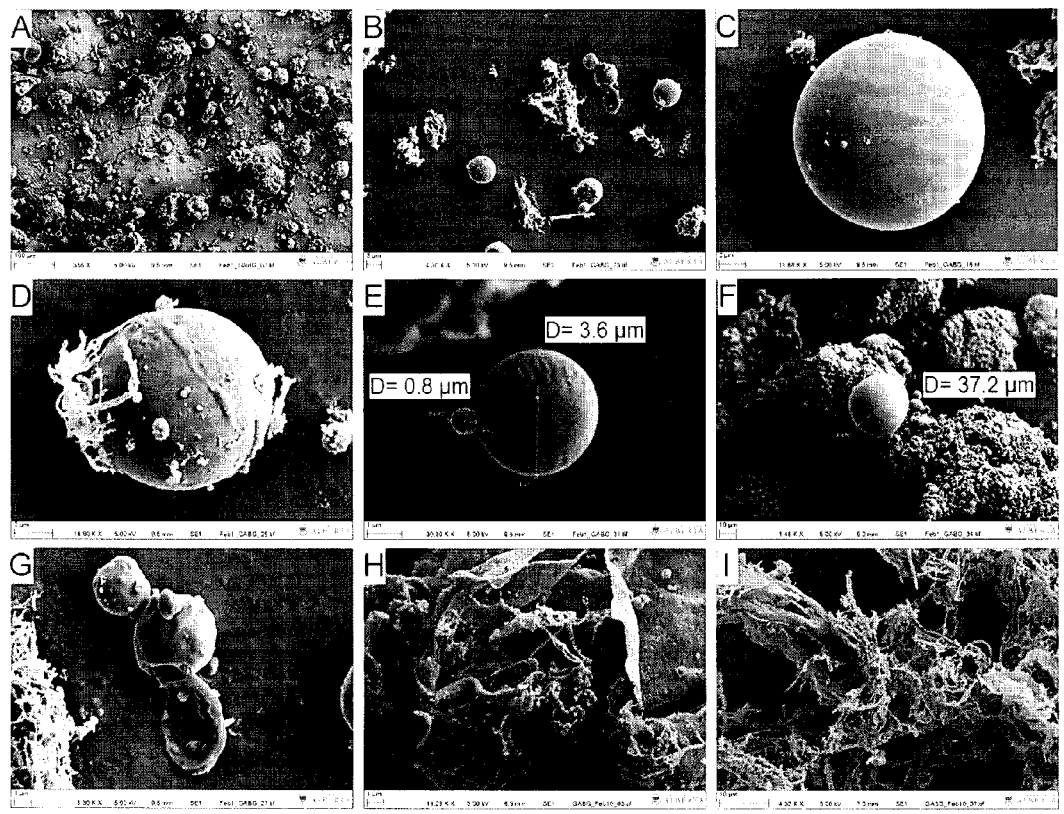
FIG. 11 shows morphologies of particles of gum arabic with β-glucan mixture (GA_BG) obtained by SFD/GAS process.
Figure 12:
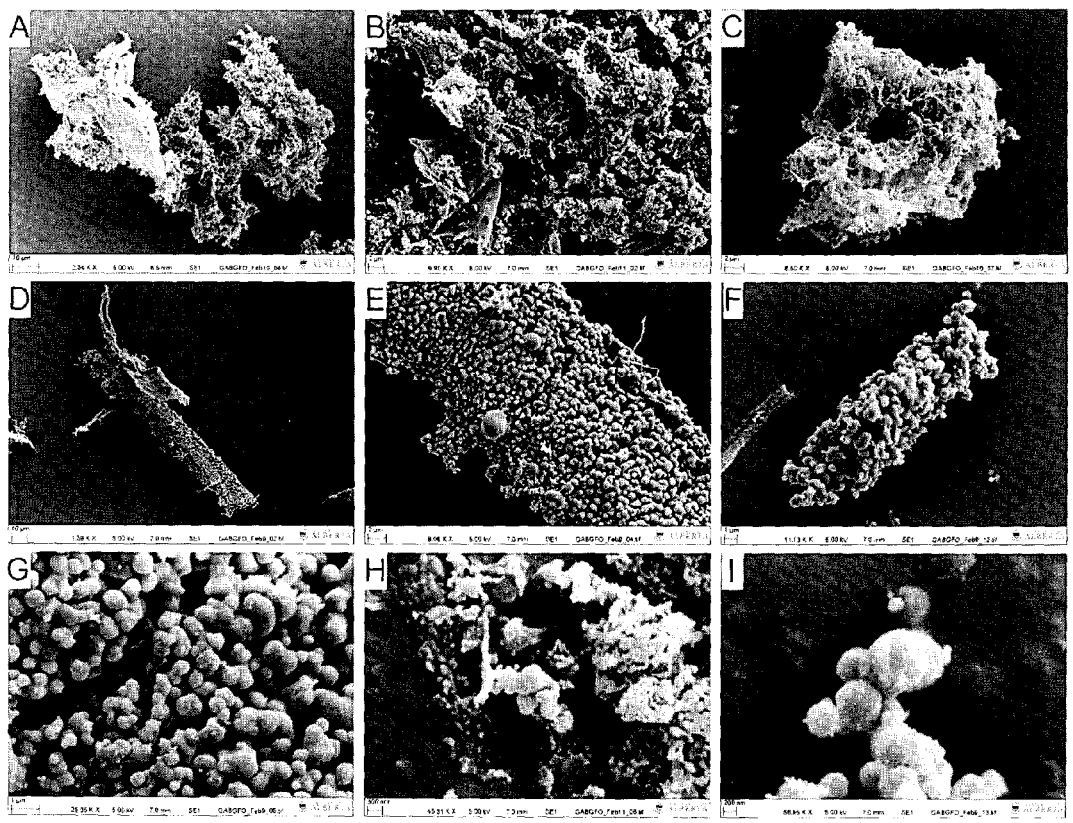
FIG. 12 shows morphologies of particles of gum arabic and β-glucan with co-injection of fish oil+EtOH+$CO_2$ (GA_BG_FO) in the SFD/GAS process.
Figure 13:
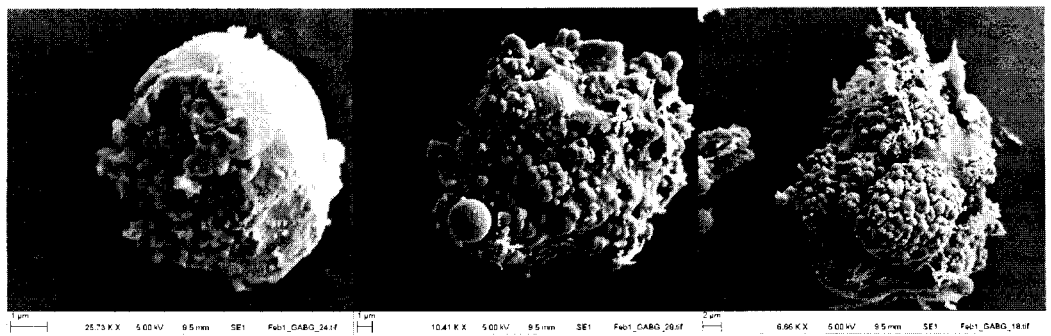
FIG. 13 shows bursting spheres with nano-globules of gum arabic and β-glucan (GA_BG).
Figure 14A:
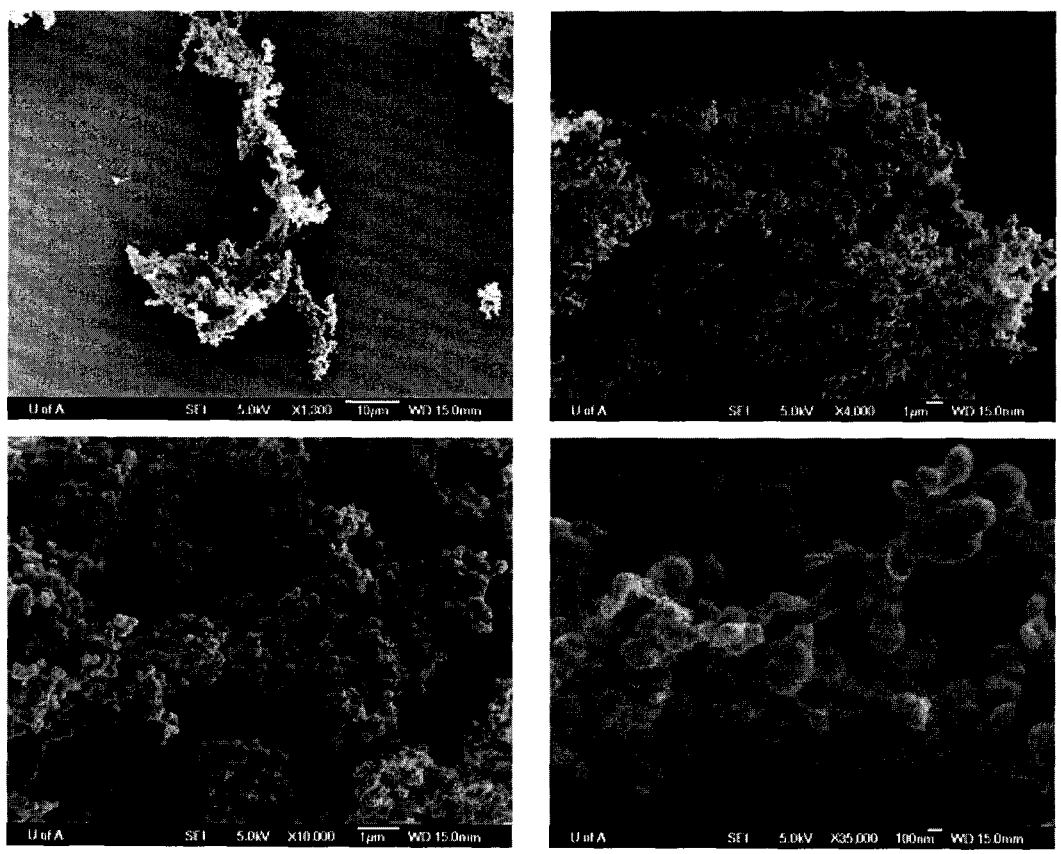
FIGS. 14A-C show images of nanosphere agglomerates of GA obtained at 10 MPa and 40° C. generated by pre-injecting 4 mL/min of antisolvent (ethanol) into the aqueous biopolymer solution prior to atomization using a coaxial nozzle and pressurized $CO_2$ at a flow rate of 25 mL/min premixed with absolute ethanol at either 16 mL/min (FIGS. 14A and 14B) or 20 mL/min (FIG. 14C).
Figure 14B:
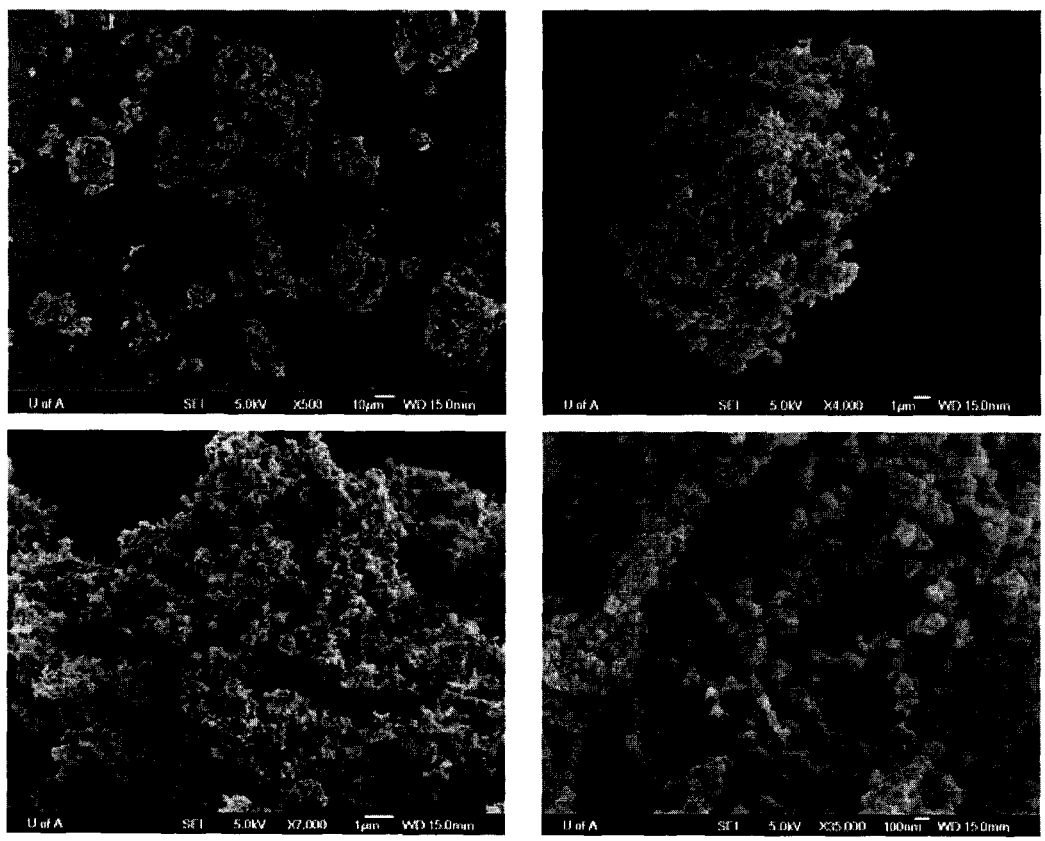
Figure 14C:
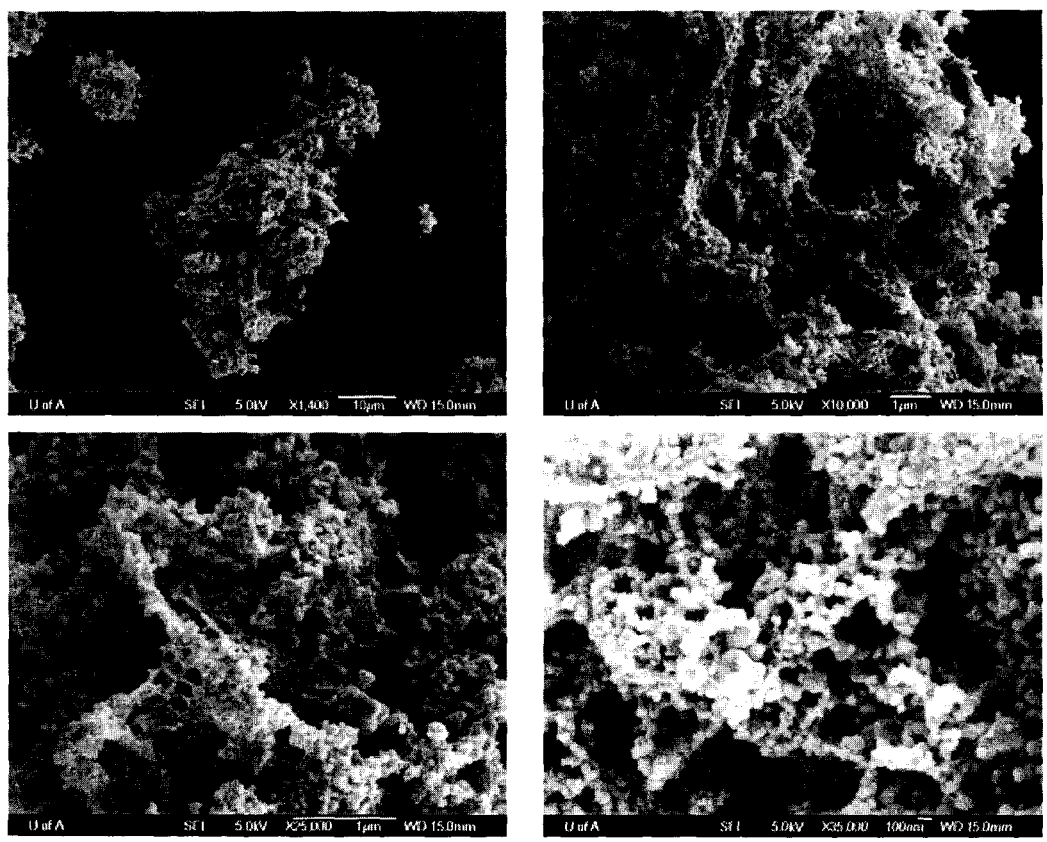
Figure 15:
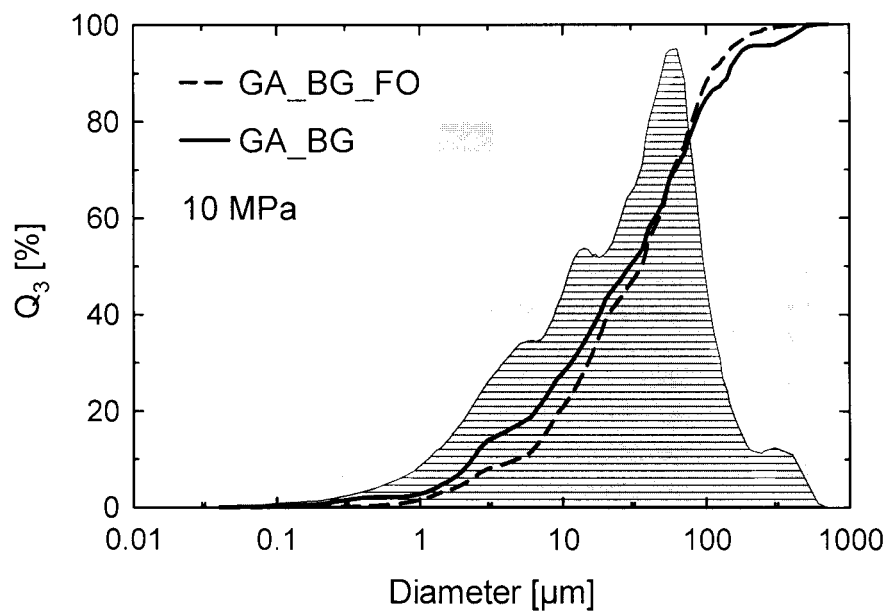
FIG. 15 shows a graph depicting particle size distribution for particles obtained at 10 MPa.
Figure 16:
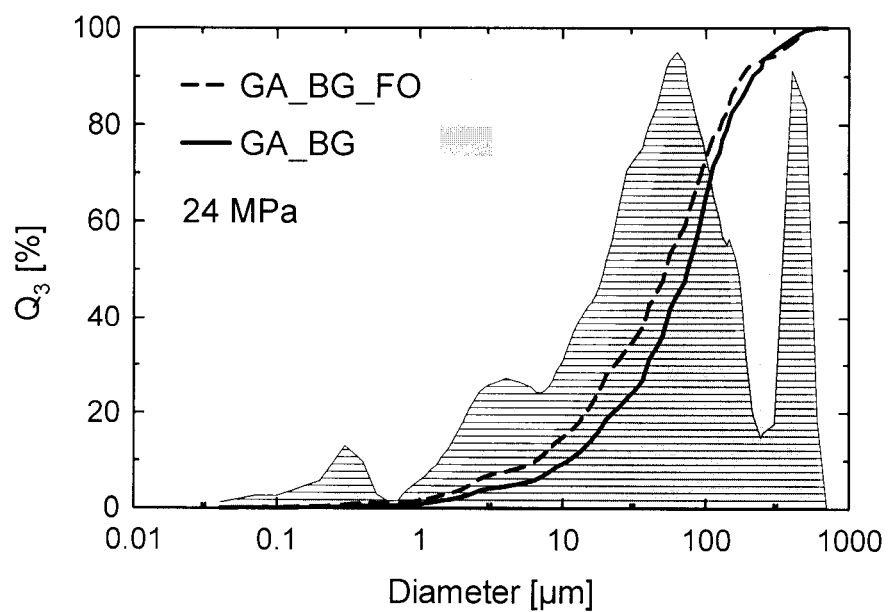
FIG. 16 shows a graph depicting particle size distribution for particles obtained at 24 MPa.
Figure 17:
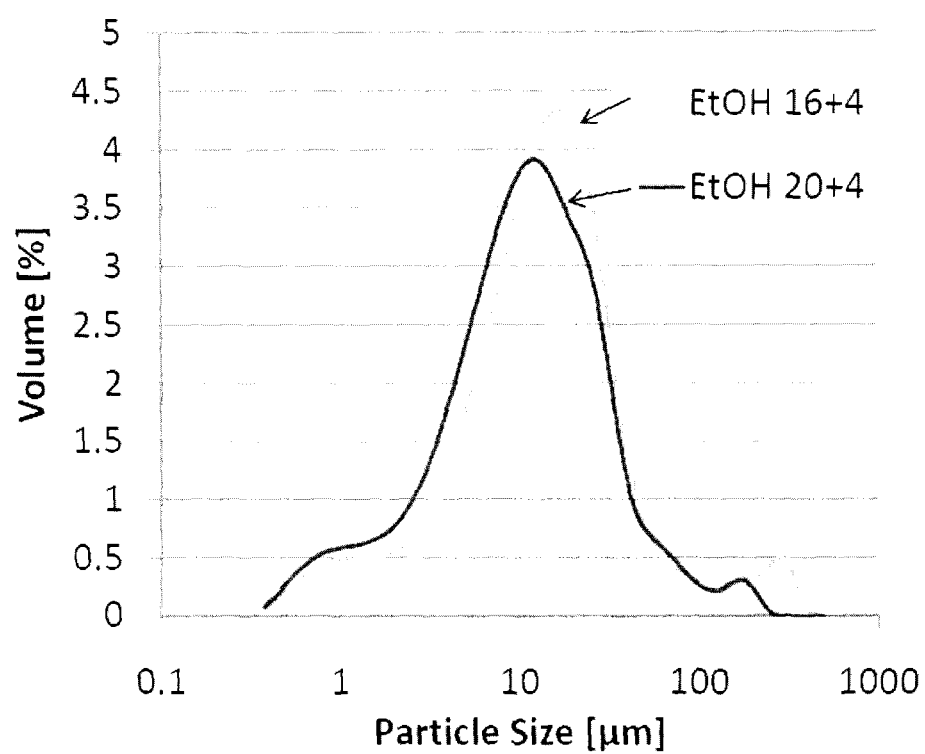
FIG. 17 shows a graph depicting particle size distributions for particles of GA generated by pre-injecting different amounts of antisolvent (ethanol) into the aqueous biopolymer solution prior to atomization.

| Experiment | Particles collected [g] | Particle bulk density [g/mL] | Appearance of precipitate | SEM images |
|---|---|---|---|---|
| GA_1 | 0.500 | 0.035 | fine voluminous powder | FIG. 7 A, B, D-I |
| GA_2 | 0.120 | 0.017 | fine voluminous powder | similar to GA_1 |
| GA_3 | 0.083 | 0.042 | fine voluminous powder | FIG. 7 C |
| BG_1 | 0.029 | 0.006 | voluminous fibrils cobweb | no SEM |
| BG_2 | 0.157 | 0.006 | voluminous fibrils cobweb | FIG. 8 A-I |
| BG_3 | 0.188 | | thicker fibrils | no SEM |
| GA_BG_1 | 0.270 | | fine voluminous powder | FIG. 9 A-G, FIG. 11 |
| GA_BG_2 | 0.055 | | fine voluminous powder | no SEM |
| GA_BG_3 | 0.965 | 0.038 | fine voluminous powder | no SEM |
| GA_BG_4 | 0.791 | | fine voluminous powder | FIG. 9 H, I |
| GA_BG_FO_1 | 0.942 | | fine voluminous powder | FIG. 10 D-G, I |
| GA_BG_FO_2 | 0.716 | 0.023 | fine voluminous powder | FIG. 10 A, C |
| GA_BG_FO_3 | 0.951 | | fine voluminous powder | FIG. 10 B, H |

Screening of Processing Parameters

Figure 4:
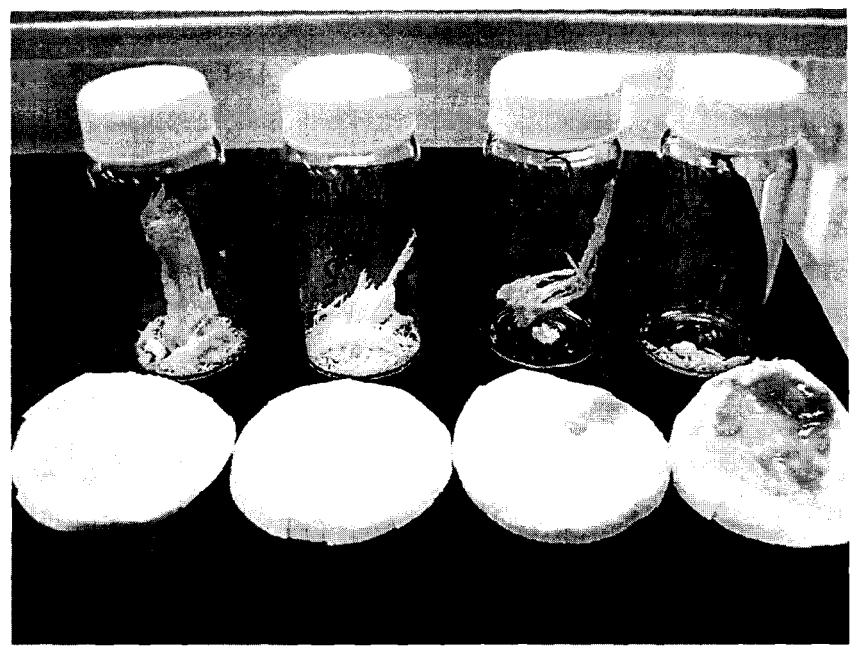
FIG. 4 shows gum arabic precipitates with nozzle configurations A and B.

In one embodiment, it was found that the maximum flow rate of the syringe pump (O) resulting in a constant continuous flow was about 25 mL/min. With that $CO_2$ flow rate and the upper limit of the HPLC pump (T) capable of delivering 24 mL/min of ethanol, it was found that the best flow rate for the relatively viscous aqueous solution was in the range of 0.9 to 1.9 mL/min. With those flow rates, the best results in terms of jet breakup, atomization and particle precipitation were achieved with the nozzle design C depicted in FIG. 2. Precipitates obtained by using the nozzle configurations FIGS. 2A and B are shown in FIG. 4. These precipitates were rod-like structures far from a powder, which was a direct result of the highly viscous solution being injected at low flow rates, thereby not forming fine droplets. Nozzle configurations shown in FIGS. 2A and B require higher flow rates for the precipitation of fine particles.

Due to the relatively high viscosity of the aqueous solutions used (for example an aqueous solution of 0.5 wt % BG concentrate had a viscosity of about 19 mPa·s at 40° C. and a shear rate of 129 $s^{-1}$), it was impossible to generate a jet breakup and fine dispersion with nozzles A and B at the very low flow rates achievable with the available pumps. Therefore, all subsequent experiments were carried out with the nozzle setup C with an orifice diameter of 0.89 mm. Furthermore, during preliminary tests, the emulsifier device consisting of the sparging element (FIG. 3A) did not prove to work well at the very low flow rates; it also caused problems during the depressurization step, since liquid was pressed out through the porous tubing, which fell onto the dry particles and destroyed the samples. Consequently, the device illustrated in FIG. 3B employing a nozzle was used for all subsequent runs.

Visual Appearance

Figure 5:
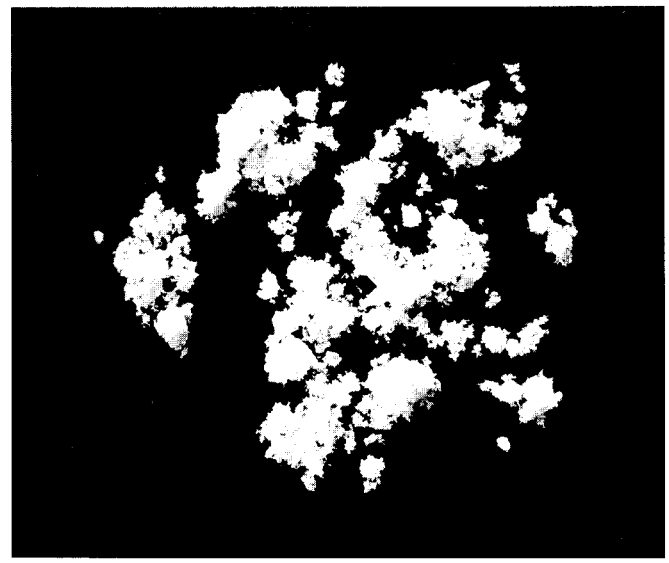
FIG. 5 shows powder of gum arabic obtained by SFD/GAS process.
Figure 6:
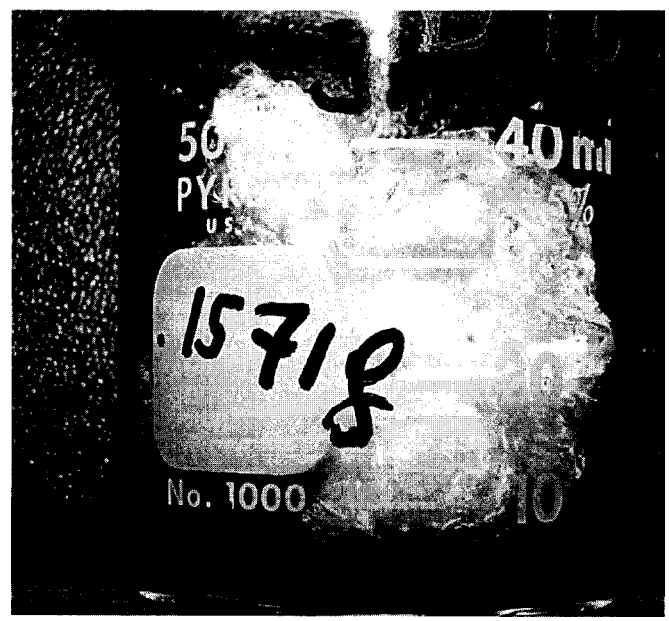
FIG. 6 shows cobweb-like structure of β-glucan (BG) obtained by SFD/GAS process.

The particles obtained in successful experiments were mostly free-flowing fluffy particles as illustrated in FIG. 5, except when pure BG solutions were sprayed, which resulted in fine fibrils and cobweb-like structures (FIG. 6). FIG. 7 shows GA particles impregnated with carotenoid-rich canola oil (CO). Impregnation of fluidized particles using pressurized $CO_2$ as atomization fluid for CO resulted in uniform impregnation, which is apparent from the bottom right image (FIG. 7). Atomization of CO was facilitated by pressurized $CO_2$ at high flow rate, which aids in fluidizing the particles and leads to a decrease in interfacial tension between CO and $CO_2$. Decrease in interfacial tension facilitates fine droplet formation, which is essential for fine dispersion and uniform impregnation.

Bulk Density

The bulk density of the obtained particles was very low, which in case of GA ranged from 0.017 to 0.042 g/mL, whereas in case of BG fibrils (FIG. 6) it was about 0.006 g/mL. Due to the very low bulk density, the processed material occupies a much larger volume than the starting material, as illustrated in FIG. 8 for GA showing the same amount of GA (0.8175 g) before and after processing.

Particle Morphology

The morphologies observed under the SEM were very diverse ranging from perfectly spherical particles, porous asymmetrical particles and amorphous structures in the case of GA (FIG. 9) to ultra-thin (<100 nm) fibrils and nanoporous sheets in the case of BG (FIG. 10). The morphology of particles obtained by co-precipitation of GA+BG resembled a mixture of fine particles both spherical and amorphous intertwined with fibrous structures (FIG. 11). The most striking particles with agglomerates of nano-spheres were obtained by the microencapsulation protocol, which may be attributed to the increased ethanol content of the total mixture prior to atomization (FIG. 12). Therefore, the antisolvent effect of ethanol on BG may have triggered local nuclei formation prior to atomization. The morphology of particles depend on the mechanism of precipitation, which can be either due to the antisolvent effect or due to spray drying effect. This was demonstrated for lysozyme precipitation in a PGSS process [20], where nitrogen-assisted atomization resulted in spherical particles, whereas $CO_2$-assisted atomization depended on the conditions in the pre-mixer since spherical particles were formed at elevated temperatures but fibrils were formed at lower temperatures. It was reported that the anti-solvent effect due to higher $CO_2$ solubility in the solvent was more pronounced [20]. Thus, if the anti-solvent effect is strong enough to induce precipitation before the atomization can take place, it is less likely to obtain spherical particles. In the case of BG, the ethanol present in the $CO_2$ phase caused a very rapid precipitation due to the anti-solvent effect, which may be the reason why BG formed mainly fibrils and sheets, whereas GA formed spheres and amorphous structures.

The exact mechanism of precipitation for GA is unknown. Without restriction to a theory, precipitation may depend on hydrodynamics in the coaxial nozzle prior to atomization and on the ethanol concentration in the $CO_2$ phase, since increased ethanol content would enhance water solubility and thus speed-up the drying process. Increased competition for water and interactions between ethanol and water would lead to having less water available to keep the polysaccharides dispersed and they would precipitate.

For the experiments with fish oil+ethanol+$CO_2$ injection, the $CO_2$ injected with the fish oil may act like a "spray enhancer" and may facilitate atomization, especially of the viscous solution and cause internal instabilities in the jet due to gas bubble formation, which leads to finer droplet formation in the coaxial nozzle and improved atomization. Agglomerates of nano-spheres were obtained in spherical and rod-like structures.

As well, some of the spheres seemed to burst and produce hollow spheres and tiny globules in experiments using a mixture of GA and BG (GA_BG) (FIG. 13).

Nanosphere agglomerates produced by presaturating the aqueous GA solution prior to atomization into the precipitation chamber consisted of nanospheres with a diameter ranging from less than 100 nm to 1 micrometer (FIGS. 14A-C).

Particle Size Distribution

The particle size distribution (PSD) was determined for the particles precipitated at 10 and 24 MPa with and without co-injection of fish oil+ethanol+$CO_2$ as illustrated in FIGS. 15 and 16, respectively. The PSD at 10 MPa shows that the particles agglomerated to larger particles in the range between 500 to 1000 μm in the case of GA_BG, while there was also a peak in the distribution in the submicron range.

Between the experiments carried out at 10 MPa and those carried out at 24 MPa an additional check valve was installed in the injection pump head (I) for the fish oil mixture, since it appeared that the internal check valves of the pump did not work properly. However, it can be clearly seen for the GA_BG powder obtained at 10 MPa that the PSD was multimodal, supporting the observations in the SEM images that the particles were very diverse non-uniform in size and agglomerated. On the other hand, the experiment at 10 MPa with co-injection of fish oil mixture resulted in a more uniform PSD. The mean particle diameter of the powders obtained at 10 MPa were substantially smaller than those obtained at 24 MPa (Table 4).

TABLE 4

Mean particle diameter for selected experimental conditions.

| Pressure [MPa] | Experimental conditions* | Diameter at 50% $Q_3$ $D_{50}$ [μm] | Mean particle diameter [μm] |
|---|---|---|---|
| 24 | GA_BG_3 | 73.2 | 117.8 |
| | GA_BG_FO_1 | 52.9 | 105.1 |
| 10 | GA_BG_4 | 29.4 | 69.6 |
| | GA_BG_FO_2 | 34.2 | 47.5 |

*refer to Table 2.

Particle size distribution of the nanosphere agglomerates showed that the mean particle diameter was influenced by the total amount of ethanol injected into the system. Ethanol injection was split between a smaller quantity (4 mL/min) injected into the aqueous GA solution pumped at 2 mL/min prior to atomization into the precipitation chamber and a larger quantity 16 or 20 mL/min injected into the pressurized $CO_2$ at 25 mL/min before reaching the coaxial nozzle for atomization and precipitation. The agglomerates with 4+20 mL/min total ethanol injected showed a smaller mean particle size of about 19 micrometer, while the precipitates generated with the 4+16 mL/min ethanol injection produced nanoparticle agglomerates with a mean particle diameter of about 27 micrometers (FIG. 17; Table 5).

TABLE 5

Effect of total amount of ethanol upon mean particle diameter
Volume Statistics (Arithmetic)
Calculations from 0.375 µm to 2000 µm

SAMPLE GA 16 + 4

| | | | |
|---|---|---|---|
| Volume: | 100% | S.D.: | 51.47 µm |
| Mean: | 27.61 µm | Variance: | 2649 µm² |
| Median: | 14.47 µm | C.V.: | 186% |
| Mean/Median ratio: | 1.907 | Skewness: | 4.534 Right skewed |
| Mode: | 18.00 µm | Kurtosis: | 22.25 Leptokurtic |

| <10% | <25% | <50% | <75% | <90% |
|---|---|---|---|---|
| 3.099 µm | 7.418 µm | 14.47 µm | 25.16 µm | 43.90 µm |
| <1 µm | <10 µm | <100 µm | <1000 µm | |
| 3.19% | 34.7% | 95.2% | 100% | |
| >1 µm | >10 µm | >100 µm | >1000 µm | |
| 96.8% | 65.3% | 4.78% | 0% | |

SAMPLE GA 20 + 4

| | | | |
|---|---|---|---|
| Volume: | 100% | S.D.: | 27.54 µm |
| Mean: | 19.11 µm | Variance: | 758.6 µm² |
| Median: | 11.55 µm | C.V.: | 144% |
| Mean/Median ratio: | 1.654 | Skewness: | 4.363 Right skewed |
| Mode: | 12.40 µm | Kurtosis: | 23.81 Leptokurtic |

| <10% | <25% | <50% | <75% | <90% |
|---|---|---|---|---|
| 2.372 µm | 5.716 µm | 11.55 µm | 21.71 µm | 36.93 µm |
| <1 µm | <10 µm | <100 µm | <1000 µm | |
| 3.80% | 44.1% | 97.6% | 100% | |
| >1 µm | >10 µm | >100 µm | >1000 µm | |
| 96.2% | 55.9% | 2.40% | 0% | |

Molecular Weight of BG Before and after Processing

The molecular weight (MW) of BG was determined before and after processing with the SFD/GAS process by means of size exclusion chromatography. The average MW of the BG molecules was in the range from 474 to 483 kDa before and 452 to 445 kDa after processing, indicating that the MW of the biopolymers is not affected substantially by the shear occurring during the SFD/GAS process. It is known to those skilled in the art that such biopolymers can be degraded by certain conventional processing operations; however, it is critical to maintain the original MW for functionality. It was surprising to find that the biopolymers were not degraded by the processing operations described herein.

Lipid Content in the Microcapsules

The lipid content of the particles was determined by first dissolving the powder (0.5 g) in 20 mL water. The powder dissolved readily in water without forming clumps, and the solution released a smell of fish oil. However, the particles did not have that distinct fish odor, which could indicate that the encapsulation was complete. Nevertheless, it appeared that very small amount of oil was present in the sample (GA_B-G_FO_3), since no fish oil appeared visible at the top of the solution. After dissolution, the lipid content of the powder was determined to be about 1% for the sample generated by experiment GA_BG_FO_3. This oil content was much lower than expected. According to the estimated oil to solid ratio injected into the system, the powder should contain around 15 to 20 wt % of fish oil. Therefore, it can be assumed that most of the oil was extracted by the $CO_2$+ethanol mixture under the conditions in the spray chamber. It would therefore be necessary to optimize the $CO_2$ pressure, and potentially reduce the ethanol content to a much lower level. Ethanol has been shown to increase triglyceride solubility in SC—$CO_2$ substantially [21], which can reach about 5 wt % in $CO_2$ at 50° C. and 10 MPa if 10 wt % of ethanol is present in $CO_2$. On the other hand, the removal of surface oil from the microcapsules due to the solvent power of $CO_2$+ethanol, thereby producing clean microcapsules can be an advantage in terms of oxidative stability of the fish oil powder.

Two potential reasons for this low oil content could be anticipated. First, the selected injection flow rate on the pump (I) was set to very low levels based on the performance of this pump for non-compressible liquids. However, the mixture of fish oil+ethanol+$CO_2$ is compressible, so that the amount of mixture injected was probably much lower than intended, which could be the main reason for the low oil load in the particles. Furthermore, part of the fish oil could have been extracted from the particles after precipitation, due to the relatively high solubility of fish oil in the SC—$CO_2$+ethanol mixture. Therefore, this process may be further optimized in order to find better processing conditions to increase the oil load in the particles and to minimize the amount of oil extracted from the capsules.

In an alternative embodiment, only a small amount of ethanol is injected in combination with the fish oil into the aqueous solution and then the charged solution is sprayed into a larger precipitation chamber with warm nitrogen as drying medium instead of $CO_2$, to avoid oil extraction from the particles after precipitation.

Solubilization Performance

In order to evaluate solubilization performance, the time required to dissolve 1 g of the BG microfibrils in 100 mL of water at various temperatures was determined and compared to that usually required to dissolve a BG powder obtained by conventional methods.

After the SFD/GAS process, the precipitated BG microfibrils were milled in a coffee grinder for about 10 seconds to disintegrate the fibrils to form free flowing fiber agglomerates of up to 5 mm in length. After milling, the bulk density of the milled microfibers was about 0.01 g/mL, thus the volume taken up by the fibers is about the same as that of a 1% (w/w) aqueous solution of the fibers. The disintegrated fibers were then used for solubilization experiments, where the time required to prepare a 1% (w/w) aqueous solution using a standard magnetic stir-plate was determined at water temperatures of 45 and 55° C.

In order to prepare a 1% (w/w) aqueous solution, 1 g of the milled microfibers were slowly added over a period of about 2 min into a beaker filled with 100 g of water at 45 and 55° C. During addition of the fibers and until complete dissolution the water was constantly heated and stirred by means of the magnetic stir-plate. The time required to fully dissolve the microfibers into water at 45 and 55° C. to obtain a clear solution with a concentration of 1% (w/w) was about 45 and 30 min, respectively. Increasing the temperature leads to a decrease in time required for solubilization.

For comparison, preparing a 1% (w/w) solution using BG powder prepared by precipitation and conventional drying can take up to several hours even when stirred into water at 80° C., which can be attributed to clumping of the powder when contacted with water and less surface area.

As will be apparent to those skilled in the art, various modifications, adaptations and variations of the foregoing specific disclosure can be made without departing from the scope of the invention claimed herein.

REFERENCES

The references are referred to herein as a numeral within a bracket, are representative of the level of skill in the art, and the contents of each are incorporated herein by reference (where permitted) as if reproduced herein in their entirety.

1. A. Shariati, C. J. Peters, Recent developments in particle design using supercritical fluids. Curr. Opin. Solid State Mater. Sci. 7 (2003) 371-383.
2. Z. Knez, E. Weidner, Particles formation and particle design using supercritical fluids. Curr. Opin. Solid State Mater. Sci. 7 (2003) 353-361.
3. J. Jung, M. Perrut, Particle design using supercritical fluids: Literature and patent survey. J. Supercrit. Fluids 20 (2001) 179-219.
4. P. York, Strategies for particle design using supercritical fluid technologies. Pharm. Sci. Technol. Today 2 (1999) 430-440.
5. F. Mattea, A. Martin, A. Matias-Gago, M. J. Cocero, Supercritical antisolvent precipitation from an emulsion: beta-Carotene nanoparticle formation. J. Supercrit. Fluids 51 (2009) 238-247.
6. N. Ventosa, S. Sala, J. Veciana, DELOS process: a crystallization technique using compressed fluids: 1. Comparison to the GAS crystallization method. J. Supercrit. Fluids 26 (2003) 33-45.
7. N. Jovanović, A. Bouchard, G. W. Hofland, G. J. Witkamp, D. J. A. Crommelin, W. Jiskoot, Stabilization of proteins in dry powder formulations using supercritical fluid technology. Pharm. Res. 21 (2004) 1955-1969.
8. A. Bouchard, N. Jovanović, W. Jiskoot, E. Mendes, G. J. Witkamp, D. J. A. Crommelin, G. W. Hofland, Lysozyme particle formation during supercritical fluid drying: Particle morphology and molecular integrity. J. Supercrit. Fluids 40 (2007) 293-307.
9. A. Bouchard, N. Jovanović, G. W. Hofland, W. Jiskoot, E. Mendes, D. J. A. Crommelin, G. J. Witkamp, Supercritical fluid drying of carbohydrates: Selection of suitable excipients and process conditions. Eur. J. Pharm. Biopharm. 68 (2008) 781-794.
10. A. Bouchard, N. Jovanović, A. H. de Boer, A. Martin, W. Jiskoot, D. J. A. Crommelin, G. W. Hofland, G. J. Witkamp, Effect of the spraying conditions and nozzle design on the shape and size distribution of particles obtained with supercritical fluid drying. Eur. J. Pharm. Biopharm. 70 (2008) 389-401.
11. A. Bouchard, N. Jovanović, A. Martin, G. W. Hofland, D. J. A. Crommelin, W. Jiskoot, G. J. Witkamp, Effect of the modifier on the particle formation and crystallisation behaviour during precipitation from aqueous solutions. J. Supercrit. Fluids 44 (2008) 409-421.
12. A. Martin, A. Bouchard, G. W. Hofland, G. J. Witkamp, M. J. Cocero, Mathematical modeling of the mass transfer from aqueous solutions in a supercritical fluid during particle formation. J. Supercrit. Fluids 41 (2007) 126-137.
13. J. Kluge, F. Fusaro, N. Casas, M. Mazzotti, G. Muhrer, Production of PLGA micro- and nanocomposites by supercritical fluid extraction of emulsions: I. Encapsulation of lysozyme. J. Supercrit. Fluids 50 (2009) 327-335.
14. J. Kluge, F. Fusaro, M. Mazzotti, G. Muhrer, Production of PLGA micro- and nanocomposites by supercritical fluid extraction of emulsions: II. Encapsulation of Ketoprofen. J. Supercrit. Fluids 50 (2009) 336-343.
15. S. Varona, S. Kareth, M. J. Cocero. Encapsulation of essentials oils using biopolymers for their use in ecological agriculture. in $9^{th}$ International symposium on supercritical fluids 2009. Arcachon, France.
16. L. Garcia-Gonzalez, A. H. Geeraerd, S. Spilimbergo, K. Elst, L. Van Ginneken, J. Debevere, J. F. Van Impe, F. Devlieghere, High pressure carbon dioxide inactivation of microorganisms in foods: The past, the present and the future. Int. J. Food Microbiol. 117 (2007) 1-28.
17. J. Zhang, T. A. Davis, M. A. Matthews, M. J. Drews, M. LaBerge, Y. H. An, Sterilization using high-pressure carbon dioxide. J. Supercrit. Fluids 38 (2006) 354-372.
18. B. S. Ghotra, T. Vasanthan, F. Temelli, Rheological properties of aqueous blends of high purity barley β-glucan with high purity commercial food gums. Food Chemistry 117 (2009) 417-425.
19. M. Sun, F. Temelli, Supercritical carbon dioxide extraction of carotenoids from carrot using canola oil as a continuous co-solvent. J. Supercrit. Fluids 37 (2006) 397-408.
20. M. A. Rodrigues, J. Li, L. Padrela, A. Almeida, H. A. Matos, E. G. de Azevedo, Anti-solvent effect in the production of lysozyme nanoparticles by supercritical fluid-assisted atomization processes. J. Supercrit. Fluids 48 (2009) 253-260.
21. G. Brunner, S. Peter, On the solubility of glycerides and fatty acids in compressed gases in the presence of an entrainer. Sep. Sci. Technol. 17 (1982) 199-214.
22. M. Perrut, J. Jung and F. Leboeuf. Method for obtaining solid particles from at least a water soluble product. United States Patent Application No. 2004/0110871, published Jun. 10, 2004.
23. M. Hanna and P. York. Method and apparatus for the formation of particles. International Publication No. WO 1995/01221, published Jan. 12, 1995.
24. M. Hanna and P. York. WO1996/00610. Method and apparatus for the formation of particles. International Publication No. WO 1996/00610, published Jan. 11, 1996.

What is claimed:

1. A method of producing micro- or nanoparticles from an aqueous solution of a biopolymer having a molecular weight of about 70 kDa or more, comprising the step of spraying the aqueous solution together with a mixture of a compressible gas and a water-soluble cosolvent/antisolvent into a pressurized chamber, wherein the cosolvent/antisolvent is present in the mixture in a concentration of 20% to 80% (w/w).

2. The method of claim 1 further comprising the step of flushing the chamber after finishing the precipitation of particles with sufficient amounts of a compressible gas to remove any residual cosolvent/antisolvent.

3. The method of claim 1 wherein the compressible gas comprises carbon dioxide, carbon dioxide and ethanol, nitrogen, or mixtures thereof.

4. The method of claim 3 wherein the water-soluble cosolvent/antisolvent comprises ethanol, acetone or isopropanol, or mixtures thereof.

5. The method of claim 1 wherein the aqueous solution and the compressible gas/cosolvent/antisolvent are sprayed into the pressurized chamber through a coaxial nozzle.

6. The method of claim 1 wherein the biopolymer comprises a polysaccharide.

7. The method of claim 6 wherein the polysaccharide comprises gum arabic or β-glucan.

8. The method of claim 1 wherein a water-soluble organic solvent is mixed with the aqueous solution prior to spraying the aqueous solution together with a mixture of a compressible gas and a water-soluble cosolvent/antisolvent into a pressurized chamber.

9. The method of claim 1 comprising the further step of flushing the chamber with a second gas having a different density than the compressible gas, to remove any residual solvents.

10. A method for microencapsulating a bioactive material with a biopolymer comprising the steps of:
a) solubilizing the bioactive in solvent comprising water or a water-soluble organic solvent, sub- or supercritical $CO_2$, a gas-expanded liquid, lipids or mixtures thereof;

b) continuously mixing the solubilized bioactive into an aqueous solution of a biopolymer to produce a mixture; and c) spraying the aqueous mixture of bioactive and biopolymer together with a mixture of a compressible gas and cosolvent/antisolvent into a pressurized chamber, wherein the concentration of the cosolvent/antisolvent in the mixture is between 20% to 80% (w/w).

11. The method of claim 10 wherein the bioactive solvent comprises water, ethanol, acetone or isopropanol, or mixtures thereof.

12. The method of claim 10 wherein the cosolvent/antisolvent comprises ethanol, acetone or isopropanol, or mixtures thereof.

13. The method of claim 10 wherein the compressible gas comprises carbon dioxide.

14. The method of claim 10 comprising the further step of flushing the chamber after finishing the precipitation of particles with sufficient amounts of the compressible gas to remove any residual solvent, or cosolvent/antisolvent.

15. The method of claim 14 comprising the further step of flushing the chamber with a second gas having a lower density than the compressible gas used in step (c) to remove any remaining solvent, or cosolvent/antisolvent to render a dry product.

16. The method of claim 1, adapted to impregnate the micro- or nanoparticles with a bioactive, comprising the further steps of:

a) solubilizing the bioactive in a suitable solvent;

b) continuously injecting the solubilized bioactive into the pressurized chamber to cause precipitation or dispersion of the bioactive on the previously formed micro- or nanoparticles without solubilizing the previously formed micro- or nanoparticles; and c) flushing the chamber with sufficient amounts of a compressible gas to remove any residual solvent.

17. The method of claim 16 wherein the flushing gas in step (c) comprises a second gas having a lower density than the compressible gas used in claim 1, to remove residuals of solvents to render a dry product.

18. The method of claim 16 wherein the bioactive comprises a material which is substantially soluble in a solvent selected from the group consisting of water, or a water-soluble organic solvent, sub- or supercritical $CO_2$, gas-expanded ethanol, lipids or mixtures thereof, and which bioactive is much less soluble in mixtures of pressurized $CO_2$ and the solvent at the conditions used for precipitating the biopolymer in claim 1.

19. The method of claim 16 wherein the solubilized bioactive is injected into the pressurized chamber at different processing conditions of pressure and/or temperature, and/or by employing another fluid mixture than that used in claim 1.

20. The method of claim 19 wherein the solubilized bioactive is injected into the pressurized chamber using pressurized nitrogen.

21. The method of claim 16, wherein the gas used in step (c) comprises pressurized nitrogen.

22. The method of claim 10 wherein the biopolymer comprises a polysaccharide.

23. The method of claim 22 wherein the polysaccharide has a molecular weight of 70 kDa or more.

24. The method of claim 23 wherein the polysaccharide comprises gum arabic or β glucan.

25. The method of claim 10 wherein the bioactive is selected from a fish oil, a plant oil, a lipid comprising mono- or polyunsaturated fatty acids, a carotenoid, a phytosterol, a tocopherol, a polyphenol, a terpenoid, an antioxidant, a peptide, a protein, a pharmaceutical substance, a nutraceutical substance, an anti-inflammatory, antimicrobial, antiviral, or antifungal agent.

26. The method of claim 25, wherein the bioactive is selected from a fish oil or a plant oil.

* * * * *